US007951799B2

(12) United States Patent
Tanaka et al.

(10) Patent No.: US 7,951,799 B2
(45) Date of Patent: May 31, 2011

(54) LACTAM COMPOUND, A METHOD FOR PRODUCING THE SAME, AND A DIABETIC THERAPY BY ADMINISTERING THE SAME

(75) Inventors: Hideyuki Tanaka, Kawasaki (JP); Wataru Miyanaga, Kawasaki (JP); Masaru Takayanagi, Kawasaki (JP); Ryusuke Hirama, Kawasaki (JP); Yoko Kageyama, Kawasaki (JP); Tatsuya Ishikawa, Kawasaki (JP); Itsuya Tanabe, Kawasaki (JP); Yoriko Okamatsu, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 725 days.

(21) Appl. No.: 11/926,745

(22) Filed: Oct. 29, 2007

(65) Prior Publication Data

US 2008/0108604 A1    May 8, 2008

Related U.S. Application Data

(63) Continuation of application No. PCT/JP2006/309349, filed on Apr. 28, 2006.

(30) Foreign Application Priority Data

Apr. 28, 2005   (JP) .................... 2005-130879

(51) Int. Cl.
*A61P 3/10*      (2006.01)
*A61K 31/55*    (2006.01)
*C07D 487/04*  (2006.01)
(52) U.S. Cl. ...................... 514/220; 540/557
(58) Field of Classification Search .................. 514/220; 540/557
See application file for complete search history.

(56) References Cited

U.S. PATENT DOCUMENTS

| 2004/0048847 A1 | 3/2004 | Iino et al. |
| 2006/0258637 A1 | 11/2006 | Hirama et al. |

FOREIGN PATENT DOCUMENTS

| EP | 1 346 993 A1 | 9/2003 |
| JP | 2004-10523 | 1/2004 |
| WO | WO 00/71506 A2 | 11/2000 |
| WO | WO 02/40485 A1 | 5/2002 |
| WO | WO 02/44180 A1 | 6/2002 |
| WO | WO 2004/069259 A1 | 8/2004 |
| WO | WO 2005/042536 A1 | 5/2005 |

OTHER PUBLICATIONS

Celia Pender, et al., "Regulation of Insulin Receptor Function by a Small Molecule Insulin Receptor Activator", The Journal of Biological Chemistry, vol. 277, No. 46, Nov. 15, 2002, pp. 43565-43571.

Khim. Farm. Zh., vol. 25, No. 11, 1991, pp. 16-18; (with English abstract) (Corresponding to: I. K. Sorokina, et al., "Search For New Drugs", Pharmaceutical Chemical Journal, vol. 25., No. 11, 1991, pp. 768-771).

Keizo Matsuo, et al., "Synthesis and Reaction of Dihydrofuro [3,4-*b*] [1,5] benzodiazepinones and Dihydropyrrolo [3,4-*b*] [1,5] benzodiazepinones", Yakugaku Zasshi, vol. 106, No. 8, 1986, pp. 715-720 (with English abstract).

Keizo Matsuo, et al., Syntheses of the Novel Furo [3,4-*b*] [1,5] benzodiazepinone and Pyrrolo [3,4-*b*] [1,5] benzodiazepinone Systems1), Chemical and Pharmaceutical Bulletin, vol. 32, No. 9, 1984, pp. 3724-3729.

Keizo Matsuo, et al., Synthesis of 10-Aryl-3,3-dimethyl-2,3,4,10-tetrahydro-1*H*-pyrrolo-[3,4-c][1,5]benzothiazepin-1-one, Yakugaku Zasshi, vol. 104, No. 9, 1984, pp. 1004-1008.(with English abstract).

Diane Grob, et al., Ring Construction Using 3-(Arylmethylene)-2,4(3H,5H)-furandione: Synthesis of Pyrazolones and Furo [3,4-c][1,5]benzothiazepinones, Journal of Organic Chemistry, vol. 48, No. 23, 1983 pp. 4367-4370.

T.P.C. Mulholland, et al. "Synthesis of Pyrrolidine-2,4-diones (Tetramic acids) and Some Derivatives", Journal of the Chemical Society Perkin Transactions 1, 1972, pp. 2121-2128.

Stylianos Hamilakis, et al., Acylaminoacetyl Derivatives of Active Methylene Compounds. 4 [1]. Synthesis of N-Protected Tetramic Acids via the C-Acylation reaction of Meldrum's Acid with the Imidazolides of N-Protected Glycines, Journal of Heterocyclic Chemistry, vol. 33, 1996, pp. 825-829.

*Primary Examiner* — Brenda L Coleman
(74) *Attorney, Agent, or Firm* — Oblon, Spivak, McClelland, Maier & Neustadt, L.L.P.

(57) ABSTRACT

The present invention provides a lactam compound, a sugar transport enhancement agent containing this compound as an active ingredient, an agent for the prevention and/or treatment of diabetes mellitus, diabetic peripheral neuropathy, diabetic nephropathy, diabetic retinopathy, diabetic macrovascular disease, glucose tolerance anomaly, obesity and the like. In addition, the present invention also provides a preparation method for the novel lactam compound, and a preparation intermediate thereof.

25 Claims, No Drawings

LACTAM COMPOUND, A METHOD FOR PRODUCING THE SAME, AND A DIABETIC THERAPY BY ADMINISTERING THE SAME

CROSS-REFERENCE TO RELATED APPLICATIONS

The present application is a continuation of PCT/JP2006/309349, filed on Apr. 28, 2006, which claims priority to Japanese Application No. JP 2005-130879, filed on Apr. 28, 2005, which are hereby incorporated by reference in their entirety.

BACKGROUND OF THE INVENTION

1. Field of the Invention

The present invention relates to a medicinal drug, and in particular, to a novel lactam compound having sugar transport enhancement action and having excellent hypoglycemic action, a preparation method thereof, and a preparation intermediate thereof.

The present invention also relates to a pharmaceutical composition comprising the lactam compound.

2. Discussion of the Background

Medicinal treatment of type II diabetes is positioned as a therapeutic method for patients for whom sufficient improvement cannot be seen by nutritional therapy or exercise therapy, and so far, formulations using insulin, which is an endogenous hormone in charge of hypoglycemic action, or peroral hypoglycemic agent having actions such as promotion of insulin secretion or improvement of peripheral insulin resistance have been developed. Currently, methods using a peroral hypoglycemic agent to adjust blood glucose stringently are the mainstream medicinal treatments of type II diabetes; however, in cases where sufficient insulin action to correct for hyperglycemia cannot be obtained, insulin therapy is carried out as major means. Meanwhile, administration of insulin therapy is the sole treatment with respect to type I diabetes, as insulin secretion capability of the patient is abolished.

Although used as an important therapy as stated above, insulin therapy, being an injectable agent, has the problems such as cumbersome procedure and education of the patients, and from the aspect of improving compliance, improvement of the administration method is strongly desired. In recent years, some attempts have been made in the development of insulin administration method by various non-injection formulations substituted for injectables; however, due to problems such as the absorption efficiency is low and the absorption does not stabilize, they are not in practical use.

As one major hypoglycemic action of insulin, the action of enhancing the sugar transport capability of peripheral cells to cause the blood sugar to be taken up by the peripheral cells, consequently decreasing the blood glucose level, may be cited. It is expected that if a novel oral medicine that would drop the blood glucose level by enhancing the sugar transport action of peripheral cells could be found, it would become a promising therapy against diabetes mellitus diseases.

As a lactam compound having the action of enhancing sugar transport of peripheral cells and having the action of decreasing the blood glucose level, compound represented by the following formula and the synthesis methods thereof are known (Patent Reference 1: International Publication WO02/44180 A1 brochure, Patent Reference 2: U.S. Patent Application Disclosure Publication US2004/0048847 A1, Patent Reference 3: International Publication WO2004/069259 A1 brochure). However, there is no concrete description of the compound of the present invention.

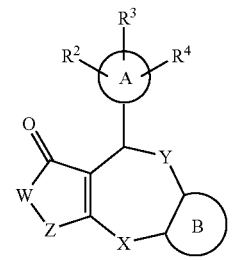

wherein A represents an aromatic ring, a heterocycle and an aliphatic ring.

In addition to the above, as compounds having the action of enhancing sugar transport of peripheral cells and having the action of decreasing blood glucose level, the compounds described in International Publication WO00/71506 A1 brochure (Patent Reference 4), International Publication WO02/40485 A1 brochure (Patent Reference 5) as well as in J. Biol. Chem. 2002, 277, 46 (15), 43565 (Non-Patent Reference 1) are known; however, they have structures that are totally different from the compound of the present invention. In addition, these are not in practical use as medicinal products.

In addition, regarding compounds having a lactam structure, several compounds have been reported (Non-Patent Reference 2: Khim. Farm. Zh. 1991, 25 (11); Non-Patent Reference 3: Pharmaceutical Chemical Journal, 1991, 25 (11), 768; Non-Patent Reference 4: pharmaceutical sciences journal, 1986, 715; Non-Patent Reference 5: Chem, Pharm. Bull. 1984, 3724; Non-Patent Reference 6: Journal of the Pharmaceutical Society of Japan, 1984, 1004; Non-Patent Reference 7: J. Org. Chem. 1983, 4367). However, they have structures that are different from the compound of the present invention, furthermore, the relationship between these compounds and the action of enhancing sugar transport of peripheral cells or the action of decreasing blood glucose level is not reported at all.

SUMMARY OF THE INVENTION

An object of the present invention is to provide an agent for the treatment of diabetes mellitus that exerts hypoglycemic action at low dose, with little side effects and having excellent physical properties as medicinal drug. In particular, among these, an object is to provide an agent for the treatment of diabetes mellitus for oral administration use having excellent membrane permeability.

An object of the present invention is to provide a novel lactam compound, or a pharmaceutically acceptable salt thereof.

An object of the present invention is to provide also a preparation method for a lactam compound containing the above-mentioned lactam compound, or a pharmaceutically acceptable salt thereof, and a preparation intermediate thereof.

An object of the present invention is to provide also a sugar transport enhancement agent.

An object of the present invention is to provide also a hypoglycemic agent.

An object of the present invention is to provide also an agent for the prevention and/or treatment of diabetes mellitus, diabetic peripheral neuropathy, diabetic nephropathy, diabetic retinopathy, diabetic macrovascular disease, glucose tolerance anomaly, or obesity.

An object of the present invention is to provide also a pharmaceutical composition.

In order to solve the above issues, the present inventors synthesized a variety of lactam compounds, found an unexpected high hypoglycemic action in a specific lactam compound having chemical structural characteristics, in having at the ring portion containing U of the following Formula (1) compound (having at the A portion of the following Formula (1-1) compound) a specific fused bicyclic heterocycle, or having at the $A_2$ portion of the following Formula (1-2) compound a specific substituted thiophene and a substituted benzene, and reached completion of the present invention. Furthermore, high membrane permeability was found in these and the present invention reached completion. By the completion of the present invention, reduction in the dosage, and the like, become possible.

That is to say, the present invention provides the following inventions.

[1] A lactam compound represented by the following Formula (1), or a pharmaceutically acceptable salt thereof.

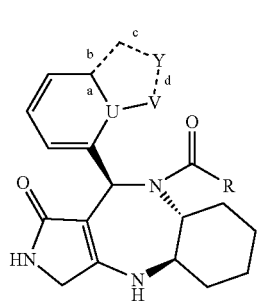

(1)

wherein R represents a lower alkyl group, a lower alkenyl group, a lower alkynyl group or a lower alkoxy group, which may have one to three substituents (chosen from Substituent Group 1 described below), Y represents either N or CR' (either NH or CHR' when the bonds indicated by c and d are both single bonds), R' represents a hydrogen atom, or a lower alkyl group, a lower alkenyl group, a lower alkynyl group, a lower alkoxy group, a lower alkylthio group, a lower alkylamino group, a halogen group, a nitro group or a cyano group, which may have one to three substituents (chosen from Substituent Group 1 described below), U represents C or N, in regard to the bonds indicated by a, b, c and d, and V, i) when U represents C, a represents a double bond, b and d represent single bonds, and c represents either a single bond or a double bond, V represents —X—, or —CH$_2$—O—, —O—CH$_2$—, —CH=N—, —N=N— or —N=CH— from the side of Y.

ii) when U represents N, a and c represent single bonds, b and d represent double bonds, V represents —N—, or —CH—X— from the side of Y, X represents O, S or NH, and the bicyclic fused ring containing U may be substituted with one to three fluorine atoms.

Substituent Group 1: halogen group, hydroxyl group, methoxy group, ethoxy group, acetoxy group, methylthio group, methane sulfonyl group, amino group, methylamino group, dimethylamino group, acetylamino group, methoxy carbamoyl group.

[2] The lactam compound as described in [1] represented by the following Formula (1-1), or a pharmaceutically acceptable salt thereof.

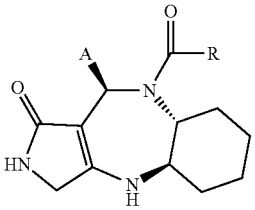

(1-1)

wherein R represents a lower alkyl group or a lower alkoxy group, which may be substituted with one to three substituents (chosen from Substituent Group 1 described in Claim 1), and A represents any of the organic groups of the following Formulae (2) to (7).

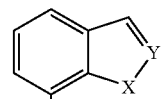

(2)

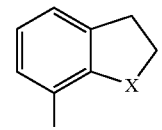

(3)

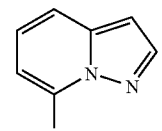

(4)

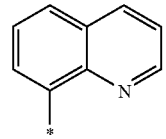

(5)

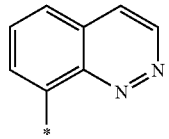

(6)

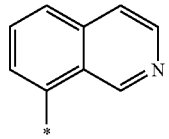

(7)

wherein, in Formulae (2) and (3), X represents O, S or NH, and Y represents N or CR'. Herein, R' represents a hydrogen atom, or a lower alkyl group, a lower alkenyl group, a lower alkynyl group, a lower alkoxy group, a lower alkylthio group, a lower alkylamino group, a halogen group, a nitro group or a cyano group, which may have 1 to 3 substituents (chosen from Substituent Group 1 described in Claim 1).

[3] The lactam compound or a pharmaceutically acceptable salt thereof as described in [2], wherein R represents a methyl group, an ethyl group, a cyclopropyl group, a hydroxymethyl group, a methoxymethyl group, a difluoromethyl group, a trifluoromethyl group or a methoxy group in Formula (1-1).

[4] The lactam compound or a pharmaceutically acceptable salt thereof as described in [2], wherein A represents an organic group represented by Formula (2), (3), (4) or (5) in Formula (1-1).

[5] The lactam compound or a pharmaceutically acceptable salt thereof as described in [2], wherein A represents an organic group represented by Formula (2) in Formula (1-1), and Y represents CR' in Formula (2).

[6] The lactam compound or a pharmaceutically acceptable salt thereof as described in [2], wherein A represents an organic group represented by Formula (2) in Formula (1-1), and Y represents CR' and R' represents a hydrogen atom or a lower alkyl group in Formula (2).

[7] The lactam compound or a pharmaceutically acceptable salt thereof as described in [2], wherein A represents an organic group represented by Formula (5) in Formula (1-1).

[8] The lactam compound or a pharmaceutically acceptable salt thereof as described in [2], wherein the compound represented by Formula (1-1) is chosen from the compound group represented by the following Formulae (a) to (j).

(a)

(b)

(c)

-continued (d)

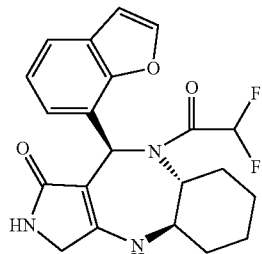

(e)

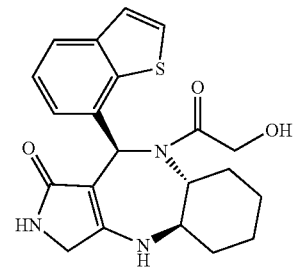

(f)

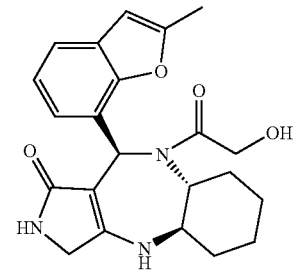

(g)

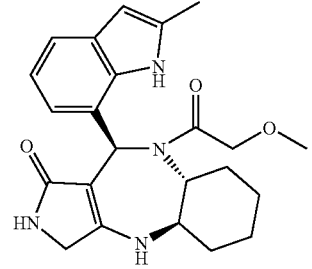

(h)

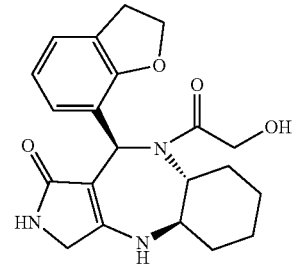

(i)

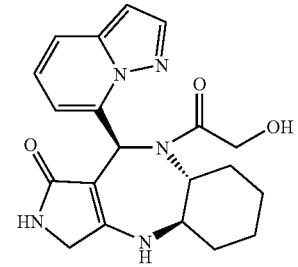

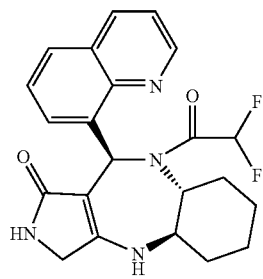

(j)

[9] The lactam compound or a pharmaceutically acceptable salt thereof as described in [8], wherein the compound represented by Formula (1-1) is the compound represented by Formula (a).

[10] The lactam compound or a pharmaceutically acceptable salt thereof as described in [8], wherein the compound represented by Formula (1-1) is the compound represented by Formula (b).

[11] The lactam compound or a pharmaceutically acceptable salt thereof as described in [8], wherein the compound represented by Formula (1-1) is the compound represented by Formula (c).

[12] The lactam compound or a pharmaceutically acceptable salt thereof as described in [8], wherein the compound represented by Formula (1-1) is the compound represented by Formula (d).

[13] The lactam compound or a pharmaceutically acceptable salt thereof as described in [8], wherein the compound represented by Formula (1-1) is the compound represented by Formula (e).

[14] The lactam compound or a pharmaceutically acceptable salt thereof as described in [8], wherein the compound represented by Formula (1-1) is the compound represented by Formula (f).

[15] The lactam compound or a pharmaceutically acceptable salt thereof as described in [8], wherein the compound represented by Formula (1-1) is the compound represented by Formula (g).

[16] The lactam compound or a pharmaceutically acceptable salt thereof as described in [8], wherein the compound represented by Formula (1-1) is the compound represented by Formula (h).

[17] The lactam compound or a pharmaceutically acceptable salt thereof as described in [8], wherein the compound represented by Formula (1-1) is the compound represented by Formula (i).

[18] The lactam compound or a pharmaceutically acceptable salt thereof as described in [8], wherein the compound represented by Formula (1-1) is the compound represented by Formula (j).

[19] A lactam compound represented by the following Formula (1-2), or a pharmaceutically acceptable salt thereof.

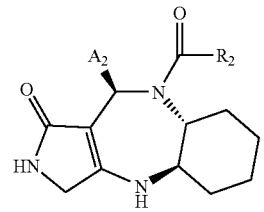

(1-2)

wherein $R_2$ represents a methyl group, an ethyl group, a cyclopropyl group, a hydroxymethyl group, a methoxymethyl group, a difluoromethyl group, a trifluoromethyl group or a methoxy group, and $A_2$ represents any of the following Formulae (2-2) and (3-2).

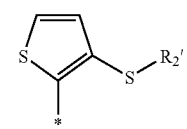

(2-2)

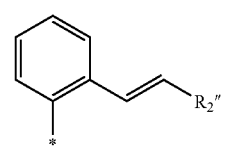

(3-2)

wherein in Formula (2-2), $R_2'$ represents a lower alkyl group and in Formula (3-2), $R_2''$ represents a hydrogen atom or a lower alkyl group.

[20] The lactam compound or a pharmaceutically acceptable salt thereof as described in [19], selected from the compound group represented by the following formulae.

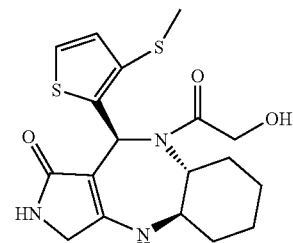

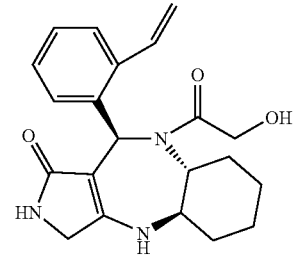

[21] A sugar transport enhancement agent comprising as an active ingredient the lactam compound or a pharmaceutically acceptable salt thereof as described in any of [1] to [20].

[22] A hypoglycemic agent comprising as an active ingredient the lactam compound or a pharmaceutically acceptable salt thereof as described in any of [1] to [20].

[23] An agent for the prevention and/or treatment of diabetes mellitus, diabetic peripheral neuropathy, diabetic nephropathy, diabetic retinopathy, diabetic macrovascular disease, glucose tolerance anomaly or obesity, comprising as an active ingredient the lactam compound or a pharmaceutically acceptable salt thereof as described in any of [1] to [20].

[24] A pharmaceutical composition comprising as an active ingredient the lactam compound or a pharmaceutically acceptable salt thereof as described in any of [1] to [20].

[25] A pharmaceutical composition comprising as an active ingredient the lactam compound or a pharmaceutically acceptable salt thereof as described in any of [1] to [20].

[26] Use of the lactam compound or a pharmaceutically acceptable salt thereof as described in any of [1] to [20], for preparing a hypoglycemic agent.

The present invention provides also the following inventions related to synthesis intermediates of a lactam compound containing Formula (1), (1-1) or (1-2) or the like

[27] A cyclohexane derivative represented by the following Formula (1-3), or a salt thereof with chemically acceptable acids.

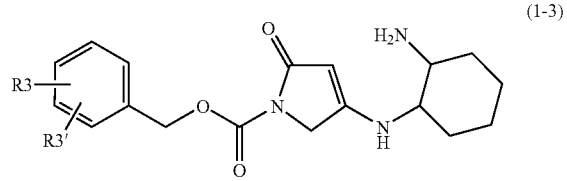

(1-3)

wherein R3 and R3' each independently represents a hydrogen atom, a nitro group, a lower alkoxy group, a halogen group or a lower alkyl group.

[28] The compound represented by the following Formula (2-3), wherein R3 and R3' represent hydrogen atoms in Formula (1-3), and the configuration of the 2-aminocyclohexylamino group portion is (1R,2R), or a salt thereof with chemically acceptable acids

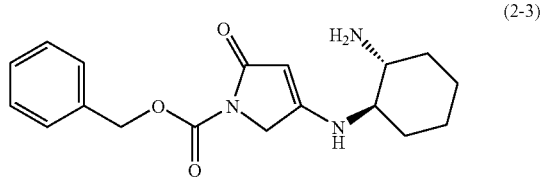

(2-3)

[29] A preparation method for the compound represented by Formula (4-3), or a salt thereof with chemically acceptable acids, wherein the compound represented by Formula (3-3) and 1,2-diaminocyclohexane are reacted.

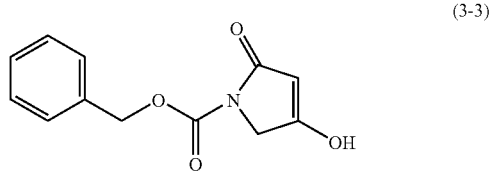

(3-3)

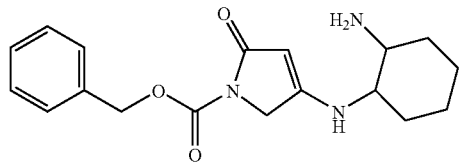

(4-3)

[30] A preparation method for the compound represented by Formula (1-3), or a salt thereof with chemically acceptable acids, wherein the compound represented by Formula (5-3) and 1,2-diaminocyclohexane are reacted.

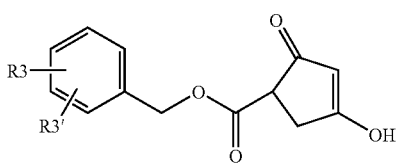

(5-3)

wherein R3 and R3' represent the same groups as those in the above Formula (1-3).

As shown in the following Test Examples, the compound represented by Formula (1), (1-1) or (1-2) has sugar transport enhancement action and high hypoglycemic action, and is useful as an agent for the prevention and/or treatment of diabetes mellitus, diabetic peripheral neuropathy, diabetic nephropathy, diabetic retinopathy, diabetic macrovascular disease, glucose tolerance anomaly or obesity.

In addition, the compound represented by Formula (1), (1-1) or (1-2) has, for instance, excellent solubility and membrane permeability, and is provided with desirable physical properties as medicinal drug. In particular, the membrane permeability being excellent, absorbability is high in oral administration, allowing the variation in blood concentration within an individual or from individual to individual to be lowered.

In addition, the compound represented by Formula (1), (1-1) or (1-2) has little side effects.

In addition, the compound represented by Formula (1), (1-1) or (1-2), and the like can be synthesized more stably via the synthesis intermediate represented by Formula (1-3).

DETAILED DESCRIPTION OF THE INVENTION

Unless specifically defined, all technical and scientific terms used herein have the same meaning as commonly understood by a skilled artisan in the relevant field (e.g., organic chemistry, pharmaceutical formulations, etc.).

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

Hereinafter, the present invention will be described in detail.

The sugar transport enhancement action in the present invention indicates an action that enhances sugar transport capability through a biological membrane, and may be an action on either the sugar transport from the external side to the internal side of a biological membrane or the sugar transport from the internal side to the external side of a biological membrane. More specifically, the action includes, for instance, insulin action, i.e., action enhancing glucose transport to the interior of muscle cells and the interior of adipocytes, and the like.

"Sugar" in sugar transport indicates pentose and hexose present in vivo. More specifically, the sugar may include, for instance glucose, mannose, arabinose, galactose, fructose, and the like, with glucose being preferred.

"May have 1 to 3 substituents" indicates cases with no substitution, or having 1 to 3 substituents, each independently selected, and in cases having substituents, if the substituents are all halogen groups, the number of substituents is preferably 2 to 3, if other than a halogen group, 1 is preferable.

"Lower alkyl group" indicates a straight chain or branched chain or cyclic alkyl group with a number of carbons of 1 to 6. More specifically, the lower alkyl groups may include, for instance, a methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, cyclopropyl group, cyclobutyl group, cyclopentyl group, cyclohexyl group, and the like. Those with a number of carbons of 1 to 3 are preferred. In particular, a methyl group, ethyl group, cyclopropyl group, and the like, are preferred.

Specific examples of "lower alkyl group that may have 1 to 3 substituents" may include, for instance, a methyl group, ethyl group, cyclopropyl group, hydroxymethyl group, 1-hydroxyethyl group, 2-hydroxyethyl group, methoxymethyl group, ethoxymethyl group, difluoromethyl group, trifluoromethyl group, and the like.

"Lower alkoxy group" indicates an alkoxy group having a straight chain or branched chain or cyclic alkyl group with a number of carbons of 1 to 6. More specifically, the lower alkoxy groups may include, for instance, a methoxy group, ethoxy group, n-propoxy group, n-butoxy group, n-pentyloxy group, n-hexyloxy group, isopropoxy group, isobutoxy group, sec-butoxy group, tert-butoxy group, cyclopropyloxy group, cyclobutoxy group, cyclopentyloxy group, cyclohexyloxy group, and the like. Those with a number of carbons of 1 to 3 are preferred. In particular, a methoxy group and ethoxy group are preferred.

"Lower alkenyl group" indicate a straight chain or branched chain or cyclic alkenyl group with a number of carbons of 1 to 6. More specifically, the lower alkenyl groups may include, for instance, vinyl group, 1-propenyl group, 2-propenyl group, isopropenyl group, 1-butenyl group, 2-butenyl group, 3-butenyl group, and the like. Those with a number of carbons of 1 to 3 are preferred. In particular, a vinyl group and 1-propenyl group are preferred.

"Lower alkynyl group" indicates a straight chain or branched chain alkynyl group with a number of carbons of 1 to 6. More specifically, the lower alkynyl groups may include, for instance, ethinyl group, 1-propynyl group, 2-propynyl group, 1-butynyl group, 2-butynyl group, 3-butynyl group, and the like. Those with a number of carbons of 1 to 3 are preferred. In particular, an ethinyl group, 1-propynyl group and 2-propynyl group are preferred.

"Lower alkylthio group" indicates an alkylthio group having a straight chain or branched chain or cyclic alkyl group with a number of carbons of 1 to 6. More specifically, the lower alkylthio groups may include, for instance, a methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group, cyclobutylthio group, and the like. Those with a number of carbons of 1 to 3 are preferred.

"Lower alkylamino group" indicates an amino group monosubstituted or disubstituted with a lower alkyl group, and as examples of this lower alkyl group, those indicated in the previous "lower alkyl group" may be cited. More specifically, the lower alkylamino groups may include, for instance, methylamino group, ethylamino group, propylamino group, isopropylamino group, dimethylamino group, diethylamino group, dipropylamino group, diisopropylamino group, methylethylamino group, and the like.

"Halogen group" represents fluorine atom, chlorine atom and bromine atom, and in particular, fluorine atom is preferred.

The "pharmaceutically acceptable salt thereof" may include, for instance, regarding the compound of the present invention that is acidic enough, ammonium salt thereof, alkaline metal salt (sodium salt, potassium salt and the like, are indicated as examples, these being referred) thereof, alkaline earth metal salt (calcium salt, magnesium salt and the like are indicated as examples, these being preferred) thereof, salt thereof with an organic base, and the like. The organic base salts may include, for example, dicyclohexyl amine salt, benzathine salt, N-methyl-D-glucan salt, hydramine salt, salt of amino acid such as arginine or lysine, and the like. Furthermore, regarding the compound of the present invention that is basic enough, the salts may include acid addition salt thereof, for instance, salt of inorganic acid, such as hydrochloric acid, sulfuric acid, nitric acid and phosphoric acid, or salt of organic acid, such as acetic acid, lactic acid, citric acid, tartaric acid, maleic acid, fumaric acid and monomethyl sulfuric acid, and the like. In addition, in some cases, the salt may be a hydrous compound or a hydrate.

In addition, the present invention includes all isomers such as optical isomers and geometric isomers, hydrates, solvates, and furthermore, mixtures thereof. Furthermore the present invention also includes prodrugs, i.e., compounds converted, in the body, to generate the lactam Compound (1), (1-1) or (1-2) of the present invention.

In the above Formula (1),

R is preferably a lower alkyl group or a lower alkoxy group, which may have 1 to 3 substituents.

In the above Formula (1-1),

The organic groups of Formulae (2) to (7) indicated by A may be further substituted with 1 to 3 substituents, in which case, the substituent is a fluorine atom, with the proviso that the organic groups having no such substituent is preferred.

As groups represented by A, preferred are the groups indicated as A in the following Table 2, regarding Examples 1 to 17.

In Formulae (2) and (3), O or NH is preferred as X, CH, C-Me or N is preferred as Y, and in particular CH or C-Me is preferred.

As group represented by R, preferred is a methyl group, ethyl group, cyclopropyl group, hydroxymethyl group, methoxymethyl group, difluoromethyl group, trifluoromethyl group or methoxy group. Among these groups, a hydroxymethyl group, methoxymethyl group or cyclopropyl group is particularly preferred, with the hydroxymethyl group being even more preferred.

Among the substituents represented in Substituent Group 1, preferred is a halogen group, hydroxyl group, methoxy group, ethoxy group, methylthio group, methylamino group or dimethylamino group. In particular, a halogen group, hydroxyl group and methoxy group are preferred.

In the above Formula (1-2),

As groups represented by $A_2$, preferred are the groups indicated by A in the following Table 2, regarding Example 18 and 19.

As groups represented by $R_2$, preferred is a methyl group, ethyl group, cyclopropyl group, hydroxymethyl group, methoxymethyl group, difluoromethyl group, trifluoromethyl group or methoxy group. Among these groups, a hydroxymethyl group, methoxymethyl group or cyclopropyl group is particularly preferred, with the hydroxymethyl group being even more preferred.

In Formula (2-2), a methyl group or ethyl group is preferred as $R_2'$, and in Formula (3-2), a hydrogen atom or methyl group is preferred as $R_2''$.

In the present invention, a compound comprising a combination of the preferred groups for each of the above symbols is preferred.

In addition, more concretely, although not limited to these, compounds described in the Examples are respectively preferred.

Hereinafter, representative preparation methods for the compounds of the present invention (1), (1-1) and (1-2) will be described.

For instance, using as starting material 4-[(1R,2R)-2-aminocyclohexylamino]-3-pyrroline-2-one (8) synthesized by the methods described later, and reacting with a corresponding aldehyde (9) by a method similar to the method described in WO02/44180 (Patent Reference 1), a cyclized Compound (10) can be obtained.

By subjecting the cyclized Compound (10) obtained in this way to acylation under generally used acylation conditions, the compounds of the present invention (1), (1-1) and (1-2), and in particular, compounds described in Examples, and the like, can be obtained.

For instance, a compound for which R in Formula (1), (1-1) or (1-2) represents an optionally substituted lower alkyl group can be synthesized, for example, by reacting the cyclized Compound (10) with the corresponding carboxylic acid using a condensation agent such as WSC.HCl {1-[3-(dimethylamino)propyl]-3-ethylcarbodiimide hydrochloride} (method A), or, by reacting with acid anhydride that is derived from carboxylic acid by a general method or commercially available, under basic conditions. When acylating, if a diacyl compound containing two acyl groups with respect to the cyclized compound (10) is partially generated as a by-product, conversion to a monoacyl compound (1), (1-1) or (1-2) is possible by subjecting the reaction products to basic treatment as is (Methods B and C). In addition, a compound in which R is a hydroxymethyl group, in particular, can be obtained by carrying out WSC condensation using acetoxy acetic acid as the corresponding carboxylic acid, then by carrying out de-protection of acetyl group by basic treatment (in cases where diacyl body is generated as by-product, at the same time as deacylation).

In addition, compounds in which R in Compound (1), (1-1) or (1-2) is a lower alkoxy group can be obtained by action on the cyclized Compound (10) of alkyl chloroformate in a hydrous solvent under basic conditions (method D).

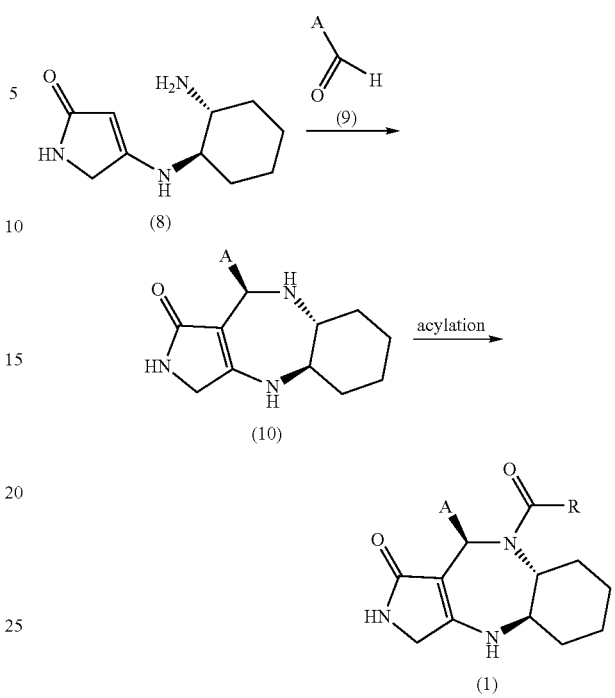

method A; RCOOH/WSC
mathod B; 1) RCOOH/WSC
    2) base/MeOH
mathod C; 1) (RCO)20/Pyridine
    2) base/MeOH
mathod D; R″OCOCl
    base/H2O/solvent Aldehyde (9) can be commercially available ones (for instance, (9c) and (9h) are commercialized by Lancaster Synthesis Ltd.), or can be obtained by using known synthesis methods as-is, or by performing a simple application thereto. For example, aldehydes (9a) to (9j) indicated in the following Table 1, can be obtained by methods described in the references indicated in the following Table 1, or the methods indicated in the Reference Examples.

TABLE 1

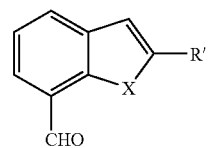

9a; X = O, R′ = H
9b; X = S, R′ = H
9c; X = NH, R′ = H
9d; X = O, R′ = Me
9e; X = NH, R′ = Me

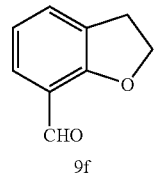

9f

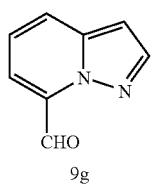

9g

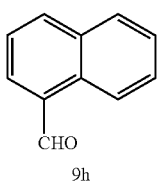

9h

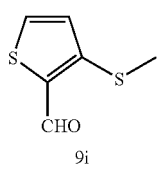

9i

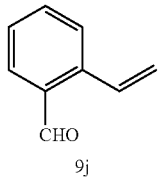

9j

| Aldehyde | Synthesis method |
|---|---|
| 9a | Benassi, Rois, J. Chem. Soc. Perkin Trans 2, 9, 1984, 1479-1486 or, Reference Example 1 |
| 9b | Noyce, D. S et.al, J. Org. Chem, 1974, 39, 2828 |
| 9d | Usha Rao et.al, Tetrahedron Lett, 24, 45, 1983, 5023-5024 or, Reference Example 2 |
| 9e | Reference Example 3 |
| 9f | Reference Example 4 |
| 9g | Gmeiner, P. et.al, J. Med. Chem, 2001, 44, 2691 |
| 9i | Onyamboko, N. V et.al, Bull. Soc. Chim. Belg, 89, 9, 1980, 773-778 |
| 9j | Kerins, F. et.al, J. Org. Chem, 2002, 67 (14), 4968-4971 |

Compound (1), (1-1) or (1-2) of the present invention can be prepared according to the above preparation methods, or by performing a simple application thereto. In addition, Compound (1), (1-1) or (1-2) of the present invention obtained by the above methods can be purified using methods used in general organic synthesis, such as, extraction, distillation, crystallization and column chromatography.

The starting material 4-(2-aminocyclohexylamino)-3-pyrroline-2-one (8) can be synthesized according to methods described in WO02/44180 (Patent Reference 1), as follows:

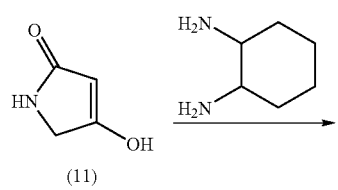

(11)

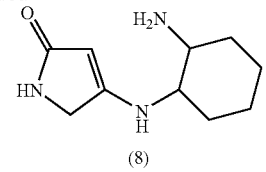

(8)

However, tetramic acid (11) is known to generate dehydration dimers readily and to be unstable (Mulholland et al., J. Chem. Soc. Perkin Trans 1, 1972, pages 2121 to 2128, Non-Patent Reference 8), such that obtaining Compound (8) stably with this method is thought to be difficult, and another method is desired.

Therefore the present inventors conducted earnest research to complete the following preparation method for Compound (8) with Compound (12) as the starting material, which can be obtained without going through tetramic acid. According to the present method, Compound (8) can be obtained more stably and with good yields, as a result, the compound of the present invention (1), (1-1) or (1-2) can be obtained more stably with good yield.

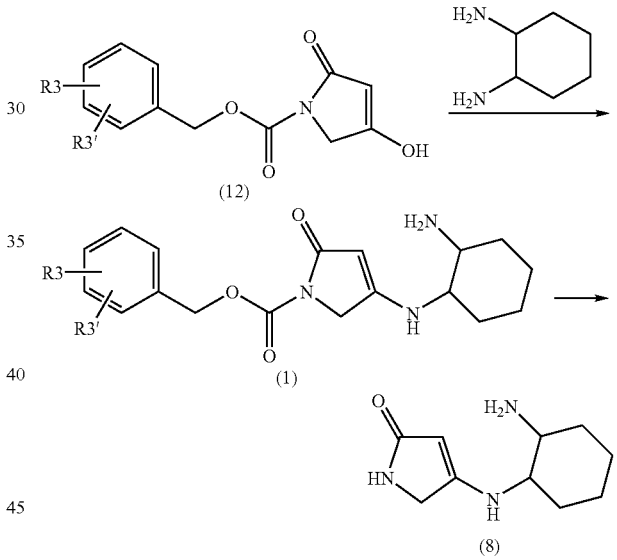

That is to say, it is a synthesis method in which Compound (12) and 1,2-diaminocyclohexane are reacted to obtain a novel synthesis Intermediate (13), then, Intermediate (13) is de-protected to obtain Compound (8).

Compound (12) can be obtained similarly to the methods described in J. Heterocyclic Chemistry, 1996, Volume 33, pages 825 to 829 (Non-Patent Reference 9). In Formula (12), hydrogen atoms are preferred as R3 and R3', and compounds in which R3 and R3' represent hydrogen atoms in Formula (12) can be prepared with N-(benzyloxycarbonyl)-glycine and Meldrum's acid as source materials.

In Formula (13), hydrogen atoms are preferred as R3 and R3', and in addition, a compound in which the configuration of the 2-aminocyclohexylamino group moiety is (1R,2R) is preferred. In addition, Compound (13) may be a salt thereof with chemically acceptable acids.

While Compound (13) can be prepared by reacting Compound (12) and 1,2-diaminocyclohexane, in so doing, although there are no particular limitations on the proportions of Compound (12) and 1,2-diaminocyclohexane, from an economic point of view, a molar ratio of 1:0.8 to 1:1.2 is preferred, and a molar ratio of 1:0.9 to 1:1.1 is more preferred.

It is preferable that acid is present in this reaction for obtaining Compound (13). In so doing, hydrogen halides such as hydrogen chloride and hydrogen bromide, sulfuric acid, nitric acid, phosphoric acid, sulfonic acids such as p-toluene sulfonic acid and methanesulfonic acid, organic acid such as acetic acid, propionic acid and succinic acid, and mixtures thereof are used as the acid, with hydrogen chloride being particularly preferred. As sources for hydrogen chloride, organic solvent solutions of hydrogen chloride gas, such as hydrogen chloride-ethyl acetate, hydrogen chloride-methanol and hydrogen chloride-dioxane can be used, and in addition, hydrochloric acid can be used. The acid may be used at a molar ratio of 0.01 or greater with respect to 1,2-diaminocyclohexane, preferably 0.8 to 1.2, and more preferably 0.9 to 1.1.

The reaction solvents may include alcohols such as methanol, ethanol, and 2-propanol, ethers such as tetrahydrofuran, dioxane and 1,2-dimethoxy ethane, esters such as ethyl acetate, isopropyl acetate, hydrocarbons such as hexane and heptane, aromatic hydrocarbons such as toluene and xylene, halogenated hydrocarbons such as dichloromethane, chloroform and chlorobenzene, nitriles such as acetonitrile and propionitrile, amides such as N,N-dimethyl formamide and N-methyl pyrrolidone, dimethylsulfoxide and mixtures thereof. From the point of view of solubility and ease of isolation of the products, alcohols, esters, and mixtures thereof are preferred. In particular, a mixture of ethanol and ethyl acetate is preferably used.

The reaction is performed in the interval from 0° C. to the boiling point of the reaction mixture. Preferably 30° C. to 80° C. is used, and more preferably 50° C. to 70° C.

Although the reaction time depends on the type of solvent and the temperature, it is roughly 1 to 24 hours. The course of the reaction can be analyzed, for instance, by high performance liquid chromatography.

Generated by the reaction, Compound (13) can be purified and isolated by such methods as solidification, crystallization, extraction and chromatography, or combination of these methods. When carrying out solidification or crystallization, performance is possible by adding a poor solvent to the solution or the mixture containing Compound (13). As poor solvent, for example, heptane, toluene, ethyl acetate, or the like, can be used. In addition, solidification or crystallization can also be carried out by cooling the solution or the mixture containing Compound (13). Furthermore, addition of poor solvent and cooling can also be used in combination. If the morphology to be isolated is free form, it is desirable to eliminate the acid used in the reaction. The methods for eliminating acid may include washing of the solution or mixture containing Compound (13) with an alkaline aqueous solution. The morphology to be isolated may be a chemically acceptable salt, in which case, isolation as a salt with the acid used in the reaction is desirable. Obviously, Compound (13) can also be subjected to the following step without isolation.

In the present specification, the chemically acceptable acids may include inorganic acid (for instance, hydrochloric acid, sulfuric acid, phosphoric acid, nitric acid, bromide hydrogen acid and the like), organic carboxylic acid (for instance, acetic acid, citric acid, benzoic acid, maleic acid, fumaric acid, tartaric acid, succinic acid, trifluoroacetic acid, tannic acid, butyric acid, hibenzoic acid, pamoic acid, enanthic acid, decanoic acid, teoclic acid, salicylic acid, lactic acid, oxalic acid, mandelic acid, malic acid and the like), and organic sulfonic acid (for instance, methane sulfonic acid, p-toluene sulfonic acid, benzene sulfonic acid and the like).

In the compound represented by Formula (13), hydrochloride is preferred. In addition, the free form is also preferred.

Compound (8) can be obtained by deprotecting Compound (13), i.e., by eliminating the benzyloxy carbonyl group. As method for deprotection, conventional methods for eliminating a benzyloxy carbonyl group can be used. For example, the deprotection method may include hydrogen reduction using a noble metal catalyst, proton transfer reaction using a noble metal catalyst and a hydrogen donor, and the like. The hydrogen reduction using a noble metal catalyst is preferred. The noble metal catalysts may include palladium catalyst, platinum catalyst, rhodium catalyst, and the like, with the palladium catalyst being preferred. As palladium catalyst, palladium black or palladium carried by various carriers can be used. For instance, the palladium catalysts may include palladium black, palladium-carbon, palladium-alumina, palladium-calcium carbonate, palladium-barium sulfate, hydroxy palladium-carbon, and the like, with the palladium carbon being preferred.

In the reaction to eliminate benzyloxy carbonyl group, the reaction solvents may include alcohols such as methanol, ethanol and 2-propanol, ethers such as tetrahydrofuran, dioxane and 1,2-dimethoxy ethane, esters such as ethyl acetate and isopropyl acetate, hydrocarbons such as hexane and heptane, aromatic hydrocarbons such as toluene and xylene, halogenated hydrocarbons such as dichloromethane, chloroform and chlorobenzene, nitriles such as acetonitrile and propionitrile, amides such as N,N-dimethyl formamide and N-methyl pyrrolidone, and mixtures thereof. From the point of view of elimination of the noble metal catalyst, preferred are alcohols which well dissolve Compound (8) that is the product, or the salt thereof, with methanol being particularly preferred.

The reaction is performed in the interval from 0° C. to the boiling point of the reaction mixture. Preferably, 10° C. to 50° C. is used, and more preferably 20° C. to 40° C.

Obtained as described above, Compound (8) or salt thereof can be purified and isolated by methods, such as solidification, crystallization, extraction and chromatography, or a combination of these methods, or can also be used as-is.

In addition, Compound (8) can be obtained readily in free form, for instance, by carrying out the above-mentioned reaction with Compound (13), which is in free form, as source material.

Further, not only the synthesized Intermediate Compound (8) can be led to the compound of the present invention (1), (1-1) or (1-2), it can also be led to the agent for the treatment of diabetes mellitus described in Patent References 1 and 2 by the methods described in Patent References 1 and 2, for instance, by reaction with benzaldehyde or substituted benzaldehyde.

The compound of the present invention (1), (1-1) or (1-2) can be converted to a pharmaceutically acceptable salt thereof by conventional methods. For instance, the methods may include mixing a compound of Formula (1), (1-1) or (1-2) and a necessary acid or base at an adequate quantity ratio in a solvent and dispersant, and carrying out cation exchange or anion exchange from another salt form.

When using the compound of the present invention as an agent for the prevention and/or treatment of diabetes mellitus, diabetic peripheral neuropathy, diabetic nephropathy, diabetic retinopathy, diabetic macrovascular disease, glucose tolerance anomaly or obesity, oral administration, intravascular administration or percutaneous administration is possible. The dosage differs depending on the symptoms and age of the patient to be administered, and the administration method, and is in general 0.001 to 1000 mg/kg/day as the amount of the active ingredient compound.

The compound of the present invention can be formulated by conventional methods. The formulation/dosage forms may include, injectable, tablet, granule, subtle granule, powdered drug, encapsulated formulation, cream agent, suppository, and the like. The formulation carriers may include, for instance, lactose, glucose, D-mannitol, crystalline cellulose, calcium carbonate, kaolin, starch, gelatin, hydroxypropyl cellulose, hydroxypropylmethyl cellulose, polyvinylpyrrolidone, ethanol, carboxymethyl cellulose, carboxymethyl cellulose calcium salt, magnesium stearate, talc, acetyl cellulose, white sugar, titanium oxide, benzoic acid, paraoxy benzoate, sodium dehydroacetate, gum arabic, tragacanth, methyl cellulose, vitelline, surfactant, white sugar, simple syrup, citric acid, distilled water, ethanol, glycerin, propylene glycol, macrogol, sodium hydrogen phosphate, sodium dihydrogen phosphate, sodium phosphate, glucose, sodium chloride, phenol, thimerosal, paraoxybenzoate ester, sodium hydrogen sulfite, and the like, and can be combined with the compound of the present invention depending upon the dosage form.

In addition, the content in active ingredient of the present invention inside the formulation of the present invention varies considerably depending on the formulation form, is not limited in particular, and is in general 0.01 to 100 percent in weight with respect to the total amount of composition, and preferably 1 to 100 percent in weight.

The compound represented by Formula (1), (1-1) or (1-2) of the present invention, has sugar transport enhancement action and high hypoglycemic action, and is useful as an agent for the prevention and/or treatment of diabetes mellitus, diabetic peripheral neuropathy, diabetic nephropathy, diabetic retinopathy, diabetic macrovascular disease, glucose tolerance anomaly, or obesity.

The above written description of the invention provides a manner and process of making and using it such that any person skilled in this art is enabled to make and use the same, this enablement being provided in particular for the subject matter of the appended claims, which make up a part of the original description. Preferred embodiments of the invention are similarly fully described and enabled.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Hereinafter, the present invention will be described in further details by means of Examples, Reference Examples and Test Examples. A further understanding can be obtained by reference to these examples, but these examples are provided herein for purposes of illustration only, and are not intended to be limiting unless otherwise specified. In addition, the structures of the compounds prepared in each Example are described later in Tables.

Reference Example 1

Synthesis of Aldehyde (9a)

(Step 1) Synthesis of 7-bromo-1-benzofuran

A suspension of potassium carbonate (50.0 g, 362 mmol) in 100 ml of DMF was added sequentially with 2-bromophenol (20.6 g, 120 mmol) and bromoacetaldehyde dimethyl acetal (20.2 g, 120 mmol) and stirred at 95° C. for 15 hours. The reaction solution was concentrated, liquid separation was carried out with ethyl acetate-water, the organic layer was sequentially washed with an aqueous solution of 1M-sodium hydroxide and saturated sodium chloride water, and dried with anhydrous magnesium sulfate. The residue obtained by concentration was dissolved in 200 ml of chlorobenzene, added at room temperature to a solution comprising diphosphorus pentoxide (8.07 g, 56.8 mmol) and 85% phosphoric acid (27 ml), which was stirred at 95° C. for 15 hours. After cooling to room temperature, the mixture was poured over ice water, stirred, and then extracted with dichloromethane. The organic layer was washed with saturated sodium chloride water and dried with anhydrous magnesium sulfate. The residue obtained by concentration was purified by silica gel chromatography (100% hexane) to obtain an oily product (10.4 g, 47%).

$^1$H-NMR (300 MHz, CDCl$_3$) δ=6.84 (1H, d, J=2.4 Hz), 7.12 (1H, t, J=7.8 Hz), 7.46 (1H, dd, J=2.4, 7.8 Hz), 7.54 (1H, dd, J=2.4, 7.8 Hz), 7.69 (1H, d, J=2.4 Hz).

(Step 2) Synthesis of Aldehyde (9a)

Magnesium powder (1.33 g, 54.7 mmol) was dried by reduced pressure while heating, cooled to room temperature, then THF was added so as to soak the magnesium. An amount of 10 mg of iodide was added, 0.45 g of Step 1 compound was gradually added, at the point when heating started, a solution of 10.0 g of Step 1 compound in 106 ml of THF was added drop-wise gradually (total Step 1 compound: 10.45 g, 53.0 mmol). The reaction solution in reflux state was heated further to 85° C. and stirred for 1.5 hours. The reaction solution was cooled to 0° C., was added with DMF (6.15 ml, 73.9 mmol), and stirred at room temperature for 30 minutes. The reaction was stopped by adding 50 ml of a saturated aqueous solution of ammonium chloride, the organic solvent was evaporated, and then liquid separation was carried out with ethyl acetate-water. The aqueous layer was extracted three times with ethyl acetate, and the pooled organic layer was washed with saturated sodium chloride water and dried with anhydrous magnesium sulfate. The residue obtained by concentration was purified by silica gel chromatography (hexane:ethyl acetate=80:20) to obtain the title compound (6.62 g, 85%).

$^1$H-NMR (300 MHz, CDCl$_3$) δ=6.87 (1H, d, J=2.4 Hz), 7.39 (1H, t, J=7.8 Hz), 7.78 (1H, d, J=2.4 Hz), 7.80 (1H, dd, J=2.4, 7.8 Hz), 7.88 (1H, dd, J=2.4, 7.8 Hz), 10.45 (1H, s).

Reference Example 2

Synthesis of Aldehyde (9d)

(Step 1) Synthesis of 2-bromophenyl propargyl ether 2-bromophenol (6.12 g, 35.3 mmol) and propargyl bromide (5.67 g, 38.1 mmol) were dissolved in DMF (34 ml). This solution was added with potassium carbonate (10.9 g, 78.9 mmol) and stirred at room temperature for 14 hours. The reaction solution was added with ethyl acetate, sequentially washed with water and saturated sodium chloride water, and dried with anhydrous sodium sulfate. Concentration under reduced pressure was carried out to obtain the title compound (7.91 g, 98.0%) as a yellow oily product.

$^1$H-NMR (300 MHz, CDCl$_3$) δ=2.54 (1H, J=2.3 Hz, t), 4.78 (2H, J=2.3 Hz, d), 6.89 (1H, J=1.5, 7.3, 7.9 Hz, ddd), 7.07 (1H, J=1.5, 8.2 Hz, dd), 7.28 (1H, J=1.8, 7.3, 8.2 Hz, ddd), 7.55 (1H, J=1.8, 7.9 Hz, dd).

(Step 2) Synthesis of 7-bromo-2-methyl-1-benzofuran

Step 1 compound (504 mg, 2.39 mmol) was dissolved in N,N-diethyl aniline (2.5 ml). This solution was added with cesium fluoride (392 mg, 2.58 mmol) and heated at 250° C. for 5 hours. The reaction solution was cooled to room temperature, then, diethyl ether was added to eliminate insoluble matter by filtration, and the filtrate was washed sequentially with 1M-hydrochloric acid and saturated sodium chloride water, and dried with anhydrous sodium sulfate. Concentration under reduced pressure, then, purification by thin layer silica gel column chromatography (100% hexane) were carried out to obtain the title compound (351 mg, 70.2%) as a yellow oily product.

$^1$H-NMR (300 MHz, CDCl$_3$) δ=2.50 (3H, J=0.9 Hz, d), 6.43 (1H, J=0.9 Hz, d), 7.04 (1H, J=7.6, 7.6 Hz, dd), 7.35 (1H, J=0.8, 7.6 Hz, dd), 7.39 (1H, J=0.8, 7.6 Hz, dd).

(Step 3) Synthesis of Aldehyde (9d)

Step 2 compound (499 mg, 2.36 mmol) was dissolved in THF (12 ml) and cooled to −78° C. This solution was added with n-butyl lithium (1.57M hexane solution, 1.66 ml, 2.61 mmol), stirred for one hour, added with DMF (0.37 ml, 4.74 mmol) and stirred at −78° C. for two and a half hours. The mixture was added with 2M-hydrochloric acid, extracted with ethyl acetate, washed with saturated sodium chloride water and dried with anhydrous sodium sulfate. Concentration under reduced pressure, then, purification by thin layer silica gel column chromatography (hexane:ethyl acetate=4:1) were carried out to obtain the target compound (346 mg, 91.1%) as a yellow oily product.

$^1$H-NMR (300 MHz, CDCl$_3$) δ=2.54 (3H, s), 6.45-6.48 (1H, m), 7.31 (1H, J=7.6 Hz, t), 7.75-7.78 (2H, m), 10.4 (1H, s).

Reference Example 3

Synthesis of Aldehyde (9e)

(Step 1) Synthesis of 2-nitrobenzaldehyde dibutyl acetal

A solution comprising 2-nitrobenzaldehyde (4.53 g, 30.0 mmol), 1-butanol (13.7 ml, 150 mmol) and toluene (60 ml) was added with p-toluene sulfonic acid monohydrate (57 mg, 0.300 mmol) and molecular sieves-4A (1 g), and refluxed for two days. The mixture was filtered through celite, washed with saturated sodium bicarbonate and saturated sodium chloride water, and then dried with anhydrous magnesium sulfate. The solution was concentrated to obtain Step 1 compound (8.43 g, quant) as a brown oily substance.

$^1$H-NMR (300 MHz, CDCl$_3$) δ=0.92 (6H, t, J=7.2 Hz), 1.32-1.45 (4H, m), 1.53-1.64 (4H, m), 3.48-3.67 (4H, m), 6.02 (1H, s), 7.45 (1H, dt, J=1.5, 8.1 Hz), 7.59 (1H, dt, J=1.2, 7.5 Hz), 7.78-7.83 (2H, m).

(Step 2) Synthesis of Aldehyde (9e)

A solution of Step 1 compound (2.81 g, 10.00 mmol) in THF (30 ml) was added with 2-propenyl magnesium bromide (0.5M-THF solution, 60.0 ml, 30.00 mmol) at −40° C. and stirred for one hour. The reaction was stopped by adding saturated ammonium chloride, 1M-hydrochloric acid (60 ml) was added, and the solution was stirred at room temperature for 15 minutes. The solution was neutralized by adding 2M-sodium hydroxide and extracted with ethyl acetate. The organic layer was washed with saturated sodium chloride water and dried with anhydrous sodium sulfate. The residue obtained by concentrating the solution was purified by silica gel column chromatography (ethyl acetate:n-hexane=1:5) to obtain the title compound (655 mg, 41%).

$^1$H-NMR (300 MHz, CDCl$_3$) δ=2.50 (3H, s), 6.28-6.30 (1H, m), 7.23 (1H, t, J=7.8 Hz), 7.56 (1H, d, J=7.8 Hz), 7.80 (1H, d, J=7.8 Hz), 9.87 (1H, brs), 10.09 (1H, s).

Reference Example 4

Synthesis of Aldehyde (9f)

(Step 1) Synthesis of 2,6-dibromo-1-(2-chloro ethoxy)benzene

A solution comprising 2,6-dibromophenol (3.90 g, 15.00 mmol), potassium carbonate (2.48 g, 17.94 mmol) and DMF (40 ml) was added with 1-bromo-2-chloro ethane (4.30 g, 29.98 mmol) and stirred at room temperature for 16 hours. The reaction solution was concentrated and liquid separation was carried out with ethyl acetate-water. The organic layer was washed with saturated sodium chloride water and dried with anhydrous sodium sulfate. The residue obtained by concentration was purified by silica gel column chromatography (n-hexane) to obtain the target compound (4.75 g, quant.) as a colorless oily substance.

$^1$H-NMR (300 MHz, CDCl$_3$) δ=3.91 (2H, t, J=6.6 Hz), 4.27 (2H, t, J=6.6 Hz), 6.89 (1H, t, J=7.8 Hz), 7.51 (2H, d, J=7.8 Hz).

(Step 2) Synthesis of Aldehyde (9f)

A solution of n-butyl lithium (1.54M-n-hexane solution, 29.2 ml, 44.97 mmol) in THF (40 ml) was added with a solution of Step 1 compound (4.75 g, 15.00 mmol) in THF (20 ml) at −40° C. and stirred for 15 minutes. Next, DMF (2.19 g, 44.97 mmol) was added and the mixture was stirred at −40° C. for 1.5 hours. The reaction was stopped by adding water, and the reaction solution was concentrated. Liquid separation was carried out with ethyl acetate-water, the organic layer was washed with 1M-hydrochloric acid and saturated sodium chloride water, dried with anhydrous sodium sulfate, and concentrated to obtain the title compound (2.32 g, quant) as a colorless crystal.

$^1$H-NMR (300 MHz, CDCl$_3$) δ=3.25 (2H, t, J=7.2 Hz), 4.74 (2H, t, J=7.2 Hz), 6.93 (1H, t, J=7.5 Hz), 7.41 (2H, d, J=7.5 Hz), 7.58 (1H, d, J=7.5 Hz), 10.20 (1H, s).

Example 1

(Step 1) Synthesis of Cyclized Compound
Compound (10a)

A solution of 4-[(1R,2R)-2-aminocyclohexylamino]-3-pyrroline-2-one (8) (115 mg, 0.589 mmol) in 5 ml of methanol was sequentially added with 7-formyl-1-benzofuran (9a) (86 mg, 0.589 mmol) and acetic acid (0.02 ml) and stirred at 50° C. for 12 hours. The main product was purified by silica gel column chromatography to obtain the cyclized compound Compound (10a) (148 mg, 78%).

Step 2

A solution of Step 1 Compound (10a) (72 mg, 0.222 mmol) in 5 ml of DMF was sequentially added with acetoxy acetic acid (263 mg, 2.22 mmol) and WSC.HCl (341 mg, 1.78 mmol), and stirred at room temperature for 14 hours. The reaction solution was concentrated, then, liquid separation was carried out with ethyl acetate-water, and the organic layer was sequentially washed with saturated sodium bicarbonate water and saturated sodium chloride water. After drying with anhydrous sodium sulfate, concentration and dissolution in 5 ml of methanol were carried out. Potassium carbonate (307 mg, 2.22 mmol) was added and the solution was stirred at room temperature for 30 minutes. The reaction solution was concentrated, then, liquid separation was carried out with ethyl acetate-water, and the organic layer was washed with saturated sodium chloride water. After drying with anhydrous sodium sulfate and concentration, the obtained residue was subjected to reverse phase HPLC having chemically bonded octadodecyl group silica gel as filler, eluted with a mixed solution of water and acetonitrile containing 0.1% (v/v) trifluoroacetic acid, and the target fraction was lyophilized to obtain Example 1 Compound (59 mg, 70%) as a white solid.

Example 2

Similarly to Example 1 Step 2, a solution of Example 1 Step 1 Compound (10a) (75 mg, 0.232 mmol) in 6 ml of DMF was sequentially added with cyclopropane carboxylic acid (0.185 ml, 2.32 mmol) and WSC.HCl (356 mg, 1.86 mmol) and stirred at room temperature for 19 hours. The reaction solution was concentrated, then, liquid separation was carried out with ethyl acetate-water, and the solution was washed with saturated sodium chloride water. After drying with anhydrous sodium sulfate and concentration, the obtained residue was subjected to reverse phase HPLC having chemically bonded octadodecyl group silica gel as filler, eluted with a mixed solution of water and acetonitrile containing 0.1% (v/v) trifluoroacetic acid, and the target fraction was lyophilized to obtain, Example 2 Compound (61 mg, 67%).

Example 3

A solution comprising Example 1 Step 1 Compound (10a) (150 mg, 0.464 mmol), 3 ml of acetonitrile and 3 ml of water was sequentially added with potassium carbonate (641 mg, 4.64 mmol) and methyl chloroformate (0.358 ml, 4.64 mmol) and stirred at room temperature for two hours. After evaporating acetonitrile, the remaining aqueous layer was extracted with dichloromethane and washed with saturated sodium chloride water. After drying with anhydrous sodium sulfate, then, concentration, purification by silica gel column chromatography were carried out to obtain Example 3 Compound (55 mg, 31%).

Example 4

A solution of Example 1 Step 1 Compound (10a) (150 mg, 0.464 mmol) in 7.5 ml of pyridine was added with anhydrous propionic acid (0.595 ml, 4.64 mmol), stirred at room temperature for 4 hours, and then stirred at 70° C. for 16 hours. After concentration and toluene azeotropy were carried out, liquid separation was carried out with dichloromethane-water, and the organic layer was washed with saturated sodium chloride water. After drying with anhydrous sodium sulfate then concentration, dissolution in 7.5 ml of methanol was carried out, potassium carbonate (321 mg, 2.33 mmol) was added, and the mixture was stirred at room temperature for two hours. After concentration, liquid separation was carried out with dichloromethane-water, and the organic layer was washed with saturated sodium chloride water. After drying with anhydrous sodium sulfate, concentration, and suspension in a mixed solvent of dichloromethane-diethyl ether, the deposited solid was filtered, and the remaining filtrate was further concentrated and purified by silica gel column chromatography to obtain Example 4 Compound (132 mg, 75%).

Example 5

(Step 1) Synthesis of Cyclized Compound
Compound (10c)

Similarly to Example 1 Step 1, a solution of 4-[(1R,2R)-2-aminocyclohexylamino]-3-pyrroline-2-one (8) (404 mg, 2.07 mmol) in 20 ml of methanol was sequentially added with 7-formyl indole (9c) (300 mg, 2.07 mmol) and acetic acid (0.059 ml), and stirred at 50° C. for 18 hours. The reaction solution was concentrated, suspended in a solution of methanol:dichloromethane=1:30, the deposited solid was filtered to obtain cyclized compound Compound (10c) (151 mg, 23%) as a white solid.

Step 2

A solution of Step 1 Compound (10c) (50 mg, 0.155 mmol) in 1 ml of DMF was sequentially added with methoxy acetic acid (0.071 ml, 0.929 mmol) and WSC.HCl (119 mg, 0.620 mmol) and stirred at room temperature for 14 hours. The reaction solution was concentrated, then, liquid separation was carried out with ethyl acetate-water, and the solution was washed with saturated sodium chloride water. After drying with anhydrous sodium sulfate and concentration, dissolution in 2.5 ml of methanol was carried out. Potassium carbonate (107 mg, 0.775 mmol) was added, and the solution was stirred at room temperature for two hours. The reaction solution was concentrated, then, neutralized with 1M-hydrochloric acid, liquid separation was carried out with ethyl acetate-water, and the organic layer was washed with saturated sodium chloride water. After drying with anhydrous sodium sulfate and concentration, purification by thin layer column chromatography was carried out to obtain Example 5 Compound (24 mg, 39%).

Example 9

(Step 1) Synthesis of Cyclized Compound
Compound (10d)

By a similar method to Example 1 Step 1, 4-[(1R,2R)-2-aminocyclohexylamino]-3-pyrroline-2-one (8) (421 mg, 2.16 mmol) was dissolved in 21 ml of ethanol instead of methanol, aldehyde (9d) (346 mg, 2.16 mmol), acetic acid (0.025 ml) were sequentially added, and the mixture was stirred at 60° C. for two hours. The reaction solution was concentrated, dichloromethane and diethyl ether were added, and the obtained solid was filtered to obtain the title compound (10d) (598 mg, 82%).

Step 2

Step 1 Compound (10d) (149 mg, 0.444 mmol) and acetoxy acetic acid (266 mg, 2.25 mmol) were dissolved in DMF (2.5 ml). This solution was added with WSC.HCl (383 mg, 2.00 mmol) and stirred at room temperature for 3 hours. Acetoxy acetic acid (159 mg, 1.35 mmol) and WSC.HCl (255 mg, 1.33 mmol) were further added and the mixture was stirred at room temperature for 13 hours. Dilution with ethyl acetate, washing with water, an aqueous solution of sodium bicarbonate and sodium chloride water, and drying with anhydrous sodium sulfate were carried out. After concentration under reduced pressure, the residue was dissolved in methanol (3.0 ml), potassium carbonate (617 mg, 4.46 mmol) was added, and the mixture was stirred at room temperature for one hour. After concentration under reduced pressure, the residue was added with water, and the deposited solid was filtered to obtain the title compound (122 mg, 69.4%).

Example 12

(Step 1) Synthesis of Cyclized Compound Compound (10e)

By a similar method to Example 1 Step 1, a solution of 4-[(1R,2R)-2-aminocyclohexylamino]-3-pyrroline-2-one (8) (782 mg, 4.01 mmol) in methanol (20 ml) was sequentially added with aldehyde (9e) (638 mg, 4.01 mmol) and acetic acid (0.046 ml, 0.800 mmol) and stirred at 50° C. for 12 hours. The reaction solution was concentrated, the obtained residue was added with methanol and dichloromethane, and the obtained solid was filtered to obtain the title compound (10e) (221 mg, 16%).

Step 2

A solution of Step 1 Compound (10e) (107 mg, 0.318 mmol) in DMF (5 ml) was added with methoxy acetic acid (0.244 ml, 3.18 mmol) and WSC.HCl (488 mg, 2.55 mmol) and stirred at room temperature overnight. The solution was further added with methoxy acetic acid (0.244 ml, 3.18 mmol) and WSC.HCl (488 mg, 2.55 mmol), stirred at room temperature overnight, further added with methoxy acetic acid (0.122 ml, 1.59 mmol) and WSC.HCl (244 mg, 1.27 mmol), stirred at room temperature overnight, then further added with methoxy acetic acid (0.244 ml, 3.18 mmol) and WSC.HCl (488 mg, 2.55 mmol) and stirred at room temperature overnight. The reaction solution was concentrated, the residue was diluted with ethyl acetate, washed with water, saturated sodium bicarbonate and saturated sodium chloride water, and then dried with anhydrous magnesium sulfate. The residue obtained by concentration was dissolved in methanol (5 ml), added with potassium carbonate (410 mg, 2.97 mmol), and the solution was stirred at room temperature for 30 minutes. Dichloromethane (15 ml) was added, the deposited insoluble matter was filtered, and the obtained filtrate was concentrated and then crudely purified by silica gel chromatography (dichloromethane:methanol=9:1). A further purification was carried out by reverse phase HPLC similarly to Example 1 Step 2 to obtain the title compound (38 mg, 37%) as a white solid.

Examples 6 to 8, 10 to 11, and 13 to 19

The compounds of Examples 6 to 8, 10 to 11, and 13 to 19 shown in Table 3 were also obtained by similar methods to Example 1 Step 1, after obtaining the closed ring compound (10) from 4-[(1R,2R)-2-aminocyclohexylamino]-3-pyrroline-2-one (8) and the corresponding aldehyde (9), and carrying out acylation using the conditions in the corresponding acylation of the above Examples 1 to 5.

During synthesis of the cyclized compound (10), if two species of diastereomers are generated as main products, the target diastereomer can be obtained by purification of the high polarity side constituent when developed with thin layer silica gel chromatography (methanol:chloroform=1:6).

Structural and physical properties data of the closed ring compounds (10) obtained as intermediates of Examples 1 to 19 are shown in Table 2. {The abbreviations in the table respectively represent: No: compound number; D: compound data; MS: ESI-MS m/z; N1: $^1$H-NMR (DMSO-d6, TMS internal standard, δ ppm); and Y: yield of the closed ring compound (10) obtained by the reaction of 4-[(1R,2R)-2-aminocyclohexylamino]-3-pyrroline-2-one (8) and corresponding aldehyde (9).}

TABLE 2

| No. | A | Y | D |
|---|---|---|---|
| 10a | 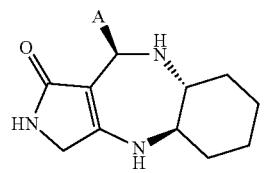 | 78 | N1: 0.75-1.20 (4 H, m), 1.35-1.55 (2 H, m), 1.75-1.90 (1 H, m), 2.10-2.25 (2 H, m), 2.75-2.90 (1 H, m), 3.72 (1 H, d, J = 16.8 Hz), 3.84 (1 H, d, J = 16.8 Hz), 5.30 (1 H, s), 6.36 (1 H, s), 6.72 (1 H, s), 6.80 (1 H, d, J = 7.5 Hz), 6.93 (1 H, d, J = 2.1 Hz), 7.09 (1 H, t, J = 7.5 Hz), 7.48 (1 H, d, J = 7.5 Hz), 7.98 (1 H, d, J = 2.1 Hz) MS: 324 (M + H)+. |

TABLE 2-continued

| No. | A | Y | D |
|---|---|---|---|
| 10b | benzothiophen-7-yl | 29 | N1: 0.79-0.90 (1 H, m), 0.96-1.14 (3 H, m), 1.39-1.54 (3 H, m), 1.84-1.91 (1 H, m), 1.94-2.06 (1 H, m), 2.76-2.86 (m, 1 H), 3.75 (1 H, J = 16.2 Hz, d), 3.91 (1 H, J =16.2 Hz, d), 5.03 (1 H, s), 6.39 (1 H, s), 6.79 (1 H, s), 6.90-6.94 (1 H, m), 7.26 (1 H, J =7.2 Hz, dd), 7.42 (1 H, J = 5.4 Hz, d), 7.69 (1 H, J = 5.4 Hz, d), 7.73 (1 H, J = 7.2 Hz, d) MS: 340 (M + H)+ |
| 10c | 1H-indol-7-yl | 23 | N1: 0.70-2.90 (11 H, m), 3.71 (1 H, d, J = 16.2 Hz), 3.87 (1 H, d, J = 16.2 Hz), 5.23 (1 H, s), 6.24 (1 H, s), 6.39 (1 H, brs), 6.58 (1 H, d, J = 7.5 Hz), 6.69 (1 H, s), 6.81 (1 H, t, J = 7.5 Hz), 7.28 (1 H, brs), 7.35 (1 H, d, J = 7.5 Hz). MS: 323 (M + H)+ |
| 10d | benzofuran-7-yl | 82 | N1: 0.78-0.98 (1 H, m), 0.99-1.23 (2 H, m), 1.38-1.71 (3 H, m), 1.76-1.95 (2 H, m), 2.15-2.27 (1 H, m), 2.47 (3 H, s), 2.80-2.92 (1 H, m), 3.73 (1 H, J = 16.4 Hz, d), 3.86 (1 H, J = 16.4 Hz, d), 4.08 (1 H, s), 5.28 (1 H, s), 6.36 (1 H, s), 6.55 (1 H, s), 6.72 (1 H, s), 6.67 (1 H, J = 7.6 Hz, d), 7.05 (1 H, J = 7.6, 7.6 Hz, dd), 7.34 (1 H, J = 7.6 Hz, d) MS: 338 (M + H)+ |
| 10e | 2-methyl-1H-indol-7-yl | 16 | N1: 0.78-0.93 (1 H, m), 0.99-1.29 (4 H, m), 1.40-1.50 (2 H, m), 1.70-1.96 (1 H, m), 2.13-2.31 (1 H, m), 2.40 (3 H, s), 2.78-2.90 (1 H, m), 3.67 (1 H, d, J = 16.5 Hz), 3.86 (1 H, d, J = 16.5 Hz), 5.22 (1 H, s), 6.09 (1 H, s), 6.23 (1 H, s), 6.52 (1 H, d, J = 7.5 Hz), 6.68 (1 H, s), 6.76 (1 H, t, J = 7.5 Hz), 7.21 (1 H, d, J = 7.5 Hz), 10.72 (1 H, s). MS: 337 (M + H)+. |
| 10f | 2,3-dihydrobenzofuran-7-yl | quant. | N1: 0.82-1.35 (5 H, m), 1.45-1.68 (2 H, m), 1.77-1.87 (1 H, m), 2.06-2.19 (1 H, m), 2.78-2.88 (1 H, m), 3.17 (2 H, t, J = 8.4 Hz), 3.69 (1 H, d, J = 16.5 Hz), 3.83 (1 H, d, J = 16.5 Hz), 4.56 (2 H, d, J = 8.4 Hz), 4.85 (1 H, s), 6.29 (1 H, s), 6.58 (1 H, d, J = 7.5 Hz), 6.65-6.70 (2 H, m), 7.07 (1 H, d, J = 7.5 Hz). MS: 326 (M + H)+. |
| 10g | pyrazolo[1,5-a]pyridin-7-yl | 60% | N1: 0.77-1.00 (2 H, m), 1.01-1.16 (3 H, m), 1.36-1.62 (2 H, m), 1.78-1.88 (1 H, m), 2.04-2.15 (1 H, m), 2.83-2.95 (1 H, m), 3.78 (1 H, J = 16.4 Hz, d), 3.89-3.94 (1 H, J =16.4 Hz, d), 5.40 (1 H, s), 6.43 (1 H, J =0.9, 6.7 Hz, d), 6.55 (1 H, s), 6.67 (1 H, J = 2.3 Hz, d), 6.83 (1 H, s), 7.17 (1 H, J = 6.7, 8.8 Hz, dd), 7.57 (1 H, J = 0.9, 8.8 Hz, dd), 8.09 (1 H, J = 2.3 Hz, d) MS: 324 (M + H)+ |
| 10h | quinolin-8-yl | 69% | N1: 0.69-0.90 (2 H, m), 0.95-1.19 (3 H, m), 1.28-1.42 (1 H, m), 1.42-1.53 (1 H, m), 1.76-1.87 (1 H, m), 2.05-2.17 (1 H, m), 2.82-2.95 (1 H, m), 3.77 (1 H, J = 16.4 Hz, d), 3.91 (1 H, J = 16.4 Hz, d), 5.82 (1 H, s), 6.37 (1 H, s), 6.94 (1 H, s), 7.24 (1 H, J = 0.9, 7.0 Hz, d), 7.48 (1 H, J = 7.0, 7.3 Hz, dd), 7.55 (1 H, J = 4.4, 8.2 Hz, dd), 7.84 (1 H, J = 0.9, 8.2 Hz, dd), 8.38 (1 H, J = 1.7, 8.2 Hz, dd), 8.96 (1 H, 1.7, 4.4 Hz, dd) MS: 335 (M + H)+ |

TABLE 2-continued

| No. | A | Y | D |
|---|---|---|---|
| 10i | (2-methylthio-thiophen-3-yl) | 42% | N1: 1.02-1.41 (4 H, m), 1.51-1.82 (4 H, m), 2.46 (3 H, s), 2.49-2.62 (1 H, m), 2.96-3.12 (1 H, m), 3.82-4.22 (2 H, m), 5.36-5.50 (1 H, m), 7.03 (1 H, d, J = 4.2 Hz), 7.09 (1 H, d, J = 4.2 Hz). MS: 336 (M + H)+. |
| 10j | (2-vinylphenyl) | 65% | N1: 0.70-3.40 (11 H, m), 3.70 (1 H, d, J = 16.2 Hz), 3.85 (1 H, d, J = 16.2 Hz), 5.02 (1 H, s), 5.29 (1 H, dd, J = 11.1, 1.5 Hz), 5.66 (1 H, dd, J = 17.7, 1.5 Hz), 6.29 (1 H, s), 6.69 (1 H, s), 6.86-6.92 (1 H, m), 7.06-7.22 (2 H, m), 7.32-7.52 (2 H, m) MS: 310 (M + H)+. |

Structural and physical properties data of Examples 1 to 19 are shown in Table 3. {The abbreviations in the table respectively represent: No: Example No.; D: compound data; MS: ESI-MS m/z, N1: $^1$H-NMR (DMSO-d6, TMS internal standard, δ ppm); and Y: yield of acylation with the corresponding closed ring compound (10) as source.}

TABLE 3

| Ex. No. | A | —R | Y | D |
|---|---|---|---|---|
| 1 | (benzofuran-7-yl) | —CH2OH | 70% | N1: 0.45-0.62 (1 H, m), 0.64-0.75 (1 H, m), 0.92-1.18 (2 H, m), 1.33-1.52 (2 H, m), 1.95-2.06 (2 H, m), 2.37-2.55 (1 H, m), 2.88 (1 H, dt, J = 4.5, 10.5 Hz), 3.82 (1 H, d, J = 16.8 Hz), 3.90 (1 H, d, J = 16.8 Hz), 3.93-4.06 (1 H, m), 4.08 (1 H, d, J = 15.3 Hz), 4.68 (1 H, d, J = 15.3 Hz), 5.83 (1 H, s), 6.85 (1 H, s), 6.99 (1 H, d, J = 2.1 Hz), 7.00 (1 H, d, J = 7.5 Hz), 7.22 (1 H, t, J = 7.5 Hz), 7.63 (1 H, d, J = 7.5 Hz), 8.05 (1 H, d, J = 2.1 Hz) MS: 382 (M + H)+ |
| 2 | (benzofuran-7-yl) | cyclopropyl | 67% | N1: 0.45-1.14 (8 H, m), 1.30-1.48 (2 H, m), 1.88-2.02 (1 H, m), 2.22-2.52 (2 H, m), 2.83-2.96 (2 H, m), 3.83 (1 H, d, J = 16.8 Hz), 3.86 (1 H, d, J = 16.8 Hz), 3.95-4.08 (1 H, m), 6.61 (1 H, s), 6.73 (1 H, s), 6.99 (1 H, d, J = 2.1 Hz), 7.03 (1 H, d, J = 7.5 Hz), 7.22 (1 H, t, J = 7.5 Hz), 7.62 (1 H, d, 1 = 7.5 Hz), 8.03 (1 H, d, J = 2.1 Hz) MS: 392 (M + H)+ |

TABLE 3-continued

| Ex. No. | A | —R | Y | D |
|---|---|---|---|---|
| 3 | benzofuran-7-yl | —OMe | 31% | N1: 0.48-2.90 (9 H, m), 3.68 (3 H, s), 3.76 (1 H, d, J = 17.4 Hz), 3.85 (1 H, d, J = 17.4 Hz), 3.71-3.89 (1 H, m), 6.38-6.52 (1 H, m), 6.66 (1 H, s), 6.76 (1 H, s), 6.92-8.03 (5 H, m). MS: 382 (M + H)+ |
| 4 | benzofuran-7-yl | —CH2CH3 | 75% | N1: 0.40-2.93 (11 H, m), 1.05 (3 H, t, J = 7.5 Hz), 3.79 (1 H, d, 1 = 16.2 Hz), 3.87 (1 H, d, J = 16.2 Hz), 3.95-4.08 (1 H, m), 6.11 (1 H, s), 6.73 (1 H, s), 6.79 (1 H, s), 6.70-8.05 (5 H, m). MS: 380 (M + H)+. |
| 5 | indol-7-yl | —CH2OMe | 39% | N1: 0.30-2.90 (9 H, m), 3.42 (3 H, s), 3.80 (1 H, d, J = 16.2 Hz), 3.89 (1 H, d, J = 16.2 Hz), 3.90-4.09 (1 H, m), 4.42-4.55 (1 H, m), 5.89 (1 H, brs), 6.46 (1 H, brs), 6.70-6.85 (3 H, m), 6.94 (1 H, t, J = 9.0 Hz), 7.37 (1 H, brs), 7.50 (1 H, d, J = 9.0 Hz), 10.38 (1 H, brs). MS: 395 (M + H)+ |
| 6 | benzofuran-7-yl | —CF2H | 65% | N1: 0.45-0.64 (2 H, m), 0.92-1.18 (2 H, m), 1.31-1.50 (2 H, m), 1.95-2.06 (1 H, m), 2.29-2.47 (1 H, m), 2.97 (1 H, dt, J = 4.5, 11.4 Hz), 3.84 (1 H, d, J = 16.5 Hz), 3.88 (1 H, d, J = 16.5 Hz), 3.92-4.01 (1 H, m), 6.18 (1 H, s), 6.87 (1 H, s), 6.88 (1 H, s), 7.00 (1 H, d, J = 2.4 Hz), 7.04 (1 H, d, J = 7.5 Hz), 7.08 (1 H, t, J = 52.8 Hz), 7.24 (1 H, t, J = 7.5 Hz), 7.65 (1 H, d, J = 7.5 Hz), 8.04 (1 H, d, J = 2.4 Hz). MS: 402 (M + H)+. |
| 7 | benzofuran-7-yl | —CF3 | 69% | N1: 0.42-0.60 (1 H, m), 0.69-0.80 (1 H, m), 0.92-1.12 (2 H, m), 1.34-1.52 (2 H, m), 1.97-2.07 (1 H, m), 2.24-2.41 (1 H, m), 3.02 (1 H, dt, J = 4.2, 11.1 Hz), 3.84 (1 H, d, J = 16.5 Hz), 3.90-4.00 (2 H, m), 6.23 (1 H, s), 6.94 (1 H, s), 6.97 (1 H, s), 7.02 (1 H, d, J = 2.4 Hz), 7.03 (1 H, d, J = 7.8 Hz), 7.26 (1 H, t, J = 7.8 Hz), 7.69 (1 H, d, J = 7.8 Hz), 8.06 (1 H, d, J = 2.4 Hz). MS: 420 (M + H)+. |
| 8 | benzothiophen-7-yl | —CH2OH | 73% | N1: 0.45-0.58 (1 H, m), 0.90-1.25 (3 H, m), 1.35-1.44 (2 H, m), 1.8-2.1 (1 H, m), 2.50-2.76 (1 H, m), 2.68-2.81 (1 H, m), 3.83 (1 H, J = 16.4 Hz, d), 3.93 (1 H, J = 16.4 Hz, d), 3.88-4.0 (2 H, m), 4.71 (1 H, J = 12 Hz, d), 5.58 (1 H, s), 6.90 (1 H, m), 7.06 (1 H, J = 5.7 Hz, d), 7.39 (m, J = 6.9 Hz, t), 7.52 (1 H, J = 5.7 Hz, t), 7.74-7.81 (1 H, m), 7.85-7.90 (1 H, m) MS: 398 (M + H)+ |

TABLE 3-continued

| Ex. No. | A | —R | Y | D |
|---|---|---|---|---|
| 9 | benzofuran-7-yl | —CH2OH | 69% | N1: 0.46-0.67 (1 H, m), 0.68-0.81 (1 H, m), 0.92-1.21 (2 H, m), 1.34-1.54 (2 H, m), 1.94-2.06 (1 H, m), 2.38-2.59 (1 H, m), 2.45 (3 H, s), 2.88-3.01 (1 H, m), 3.80 (d, J = 16.4 Hz, 1 H), 3.93 (d, J = 16.4 Hz, 1 H), 3.93-4.05 (1 H, m), 4.09 (1 H, J = 4.4, 15.2 Hz, dd), 4.53 (1 H, J = 4.4 Hz, t), 4.65 (1 H,. J = 4.4, 15.2 Hz, dd), 5.80 (1 H, s), 6.60 (1 H, s), 6.82 (1 H, s), 6.82 (1 H, s), 6.90 (1 H, J = 7.3 Hz, d), 7.14 (1 H., J = 7.3, 7.3 Hz, dd), 7.48 (1 H, J = 7.3 Hz, d) MS: 396 (M + H)+ |
| 10 | benzofuran-7-yl | —CH2OMe | 56% | N1: 0.44-0.64 (1 H, m), 0.65-0.77 (1 H, m), 0.91-1.14 (2 H, m), 1.32-1.54 (2 H, m), 1.92-2.08 (1 H, m), 2.37-2.45 (1 H, m), 2.45 (3 H, s), 2.89 (1 H, J = 4.1, 11.1 Hz, dt), 3.80 (1 H, J = 16.4 Hz, d), 3.87 (1 H, J = 16.4 Hz, d), 3.96-4.08 (1 H, m), 4.22 (1 H, J = 14.7 Hz, d), 4.56 (1 H, J = 14.7 Hz, d), 5.93 (1 H, s), 6.60 (1 H, s), 6.79 (1 H, s), 6.79 (1 H, s), 6.90 (1 H, J = 7.3 Hz, d), 7.13 (1 H, J = 7.3, 7.3 Hz, dd), 7.49 (1 H, J = 7.3 Hz, d) MS: 410 (M + H)+ |
| 11 | indol-7-yl | —CH2OH | 47% | N1: 0.36-0.58 (1 H, m), 0.76-1.18 (3 H, m), 1.31-1.49 (2 H, m), 1.89-2.02 (1 H, m), 2.24-2.46 (4 H, m), 2.83-2.95 (1 H, m), 3.80 (1 H, d, J = 16.5 Hz), 3.88-4.07 (3 H, m), 4.56 (1 H, d, J = 13.2 Hz), 6.01 (1 H, s), 6.16 (1 H, s), 6.69 (1 H, d, J = 7.5 Hz), 6.74 (1 H, s), 6.89 (1 H, t, J = 7.5 Hz), 7.36 (1 H, d, J = 7.5 Hz), 10.57 (1 H, s). MS: 395 (M + H)+. |
| 12 | indol-7-yl | —CH2OMe | 37% | N1: 0.35-0.57 (1 H, m), 0.73-1.18 (3 H, m), 1.30-1.49 (2 H, m), 1.91-2.05 (1 H, m), 2.27-2.48 (4 H, m), 2.82-2.96 (1 H, m), 3.47 (3 H, s), 3.80 (1 H, d, J = 16.5 Hz), 3.86-4.10 (3 H, m), 4.41 (1 H, J = 12.0 Hz), 5.90 (1 H, s), 6.18 (1 H, s), 6.69 (1 H, d, J = 7.5 Hz), 6.76 (1 H, s), 6.90 (1 H, t, J = 7.5 Hz), 7.37 (1 H, d, J = 7.5 Hz), 10.13 (1 H, s). MS: 409 (M + H)+. |
| 13 | 2,3-dihydrobenzofuran-7-yl | —CH2OH | 48% | N1: 0.57-0.76 (1 H, m), 0.91-1.10 (3 H, m), 1.41-1.56 (2 H, m), 1.92-2.06 (1 H, m), 2.28-2.61 (1 H, m), 2.90 (1 H, dt, J = 4.5, 11.4 Hz), 3.19 (2 H, t, J = 8.4 Hz), 3.78 (1 H, d, J = 15.9 Hz), 3.82 (1 H, d, J = 15.9 Hz), 3.86-4.03 (2 H, m), 4.34 (1 H, t, J = 4.8 Hz), 4.42-4.63 (3 H, m), 5.37 (1 H, s), 6.67-6.79 (4 H, m), 7.19 (1 H, t, J = 4.2 Hz). MS: 384 (M + H)+. |

TABLE 3-continued

| Ex. No. | A | —R | Y | D |
|---|---|---|---|---|
| 14 | pyrazolo[1,5-a]pyridin-7-yl | —CH2OH | 19% | N1: 0.527-0.723 (2 H, m), 1.03-1.14 (2 H, m), 1.33-1.55 (2 H, m), 1.98-2.07 (1 H, m), 2.32-2.47 (1 H, m), 2.95-3.08 (1 H, m), 3.81 (1 H, J = 16.7 Hz, d), 3.93 (1 H, J = 16.7 Hz, d), 3.96-4.11 (2 H, m), 4.49 (1 H, J = 5.3 Hz, t), 5.05 (1 H, J = 5.3, 15.5 Hz, dd), 5.97 (1 H, s), 6.73 (1 H, J = 2.3 Hz, d), 6.76 (1 H, s), 6.91 (1 H, s), 6.95-6.98 (1 H, m), 7.24 (1 H, J = 6.8, 8.8 Hz, dd), 7.75 (1 H, J = 8.8 Hz, d), 8.10 (1 H, J = 2.3 Hz, d) MS: 382 (M + H)+ |
| 15 | pyrazolo[1,5-a]pyridin-7-yl | —CH2OMe | 43% | N1: 0.45-3.10 (9H, m), 3.32 (3 H, s), 3.81 (1 H, d, J = 16.5 Hz), 3.87 (1 H, d, J = 16.5 Hz), 3.95-4.10 (1 H, m), 4.34 (1 H, d, J = 14.1 Hz), 4.81 (1 H, d, J = 14.1 Hz), 6.05 (1 H, s), 6.68-6.76 (2 H, m), 6.85 (1 H, s), 6.88 (1 H, s), 7.18-7.26 (1 H, m), 7.70-7.76 (1 H, m), 8.06-8.12 (1 H, m). MS: 396 (M + H)+. |
| 16 | quinolin-8-yl | —CH2OH | 70% | N1: 0.40-0.58 (2 H, m), 1.00-1.10 (2 H, m), 1.2-1.3 (1 H, m), 1.39-1.46 (1 H, m), 1.94-2.02 (1 H, m), 2.25-2.40 (1 H, m), 2.98 (1 H, J = 3.0, 4.2, 12 Hz, ddd), 3.80 (1 H, J = 16 Hz, d), 3.89 (1 H, J = 16 Hz, d), 3.95-4.03 (1 H, m), 4.09 (1 H, J = 5.1, 15 Hz, dd), 4.42 (1 H, J = 5.1 Hz, d, OH), 5.19 (1 H, J = 5.1, 15 Hz, dd), 6.40 (1 H, s), 6.78 (1 H, s), 6.80 (1 H, s), 7.49-7.60 (3 H, s), 7.95 (1 H, J = 1.8, 8.1 Hz, dd), 8.40 (1 H, J = 1.5, 5.7 Hz, dd), 8.90 (1 H, J = 1.8, 4.2 Hz, dd) MS: 393 (M + H)+ |
| 17 | quinolin-8-yl | —CF2H | 61% | N1: 0.30-0.42 (1 H, m), 0.48-0.67 (1 H, m), 0.97-1.18 (2 H, m), 1.26-1.37 (1 H, m), 1.40-1.50 (1 H, m), 1.99-2.08 (1 H, m), 2.18-2.35 (1 H, m), 3.14 (1 H, dt, J = 4.8, 10.8 Hz), 3.84 (1 H, d, J = 16.2 Hz), 3.41 (1 H, d, J = 16.2 Hz), 3.93-4.04 (1 H, m), 6.64 (1 H, d, J = 3.0 Hz), 6.84 (1 H, s), 6.84 (1 H, s), 7.56-7.65 (3 H, m), 7.74 (1 H, t, J = 54.0 Hz), 8.01 (1 H, dd, J = 7.5, 1.8 Hz), 8.45 (1 H, dd, J = 8.1, 1.8 Hz), 8.98 (1 H, dd, J = 7.5, 1.8 Hz). MS: 413 (M + H)+. |
| 18 | 3-(methylthio)thiophen-2-yl | —CH2OH | 59% | N1: 0.61-0.80 (1 H, m), 0.92-1.23 (2 H, m), 1.25-1.37 (1 H, m), 1.44-1.60 (2 H, m), 1.93-2.06 (1 H, m), 2.37-2.62 (4 H, m), 2.93-3.05 (1 H, m), 3.68-4.01 (4 H, m), 4.51 (1 H, t, J = 4.8 Hz), 4.63 (1 H, d, J = 15.3 Hz), 5.41 (1 H, s), 6.83 (1 H, s), 6.90 (1 H, s), 7.15 (1 H, d, J = 5.4 Hz), 7.46 (1 H, dd, J = 5.4, 1.2 Hz). MS: 394 (M + H)+. |

TABLE 3-continued

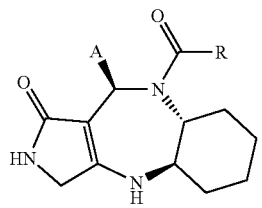

| Ex. No. | A | —R | Y | D |
|---|---|---|---|---|
| 19 | ![styrene] | —CH2OH | 39% | N1: 0.40-3.40 (9 H, m), 3.70-4.02 (4 H, m), 4.39-4.64 (2 H, m), 5.39-5.41 (1 H, m), 5.47 (1 H, brs), 5.67 (1 H, d, J = 18.0 Hz), 6.70-7.60 (7 H, m). MS: 368 (M + H)+ |

Example 20

Synthesis of 4-[(1R,2R)-2-aminocyclohexylamino]-2-oxo-3-pyrroline-1-carboxylic acid benzyl ester hydrochloride

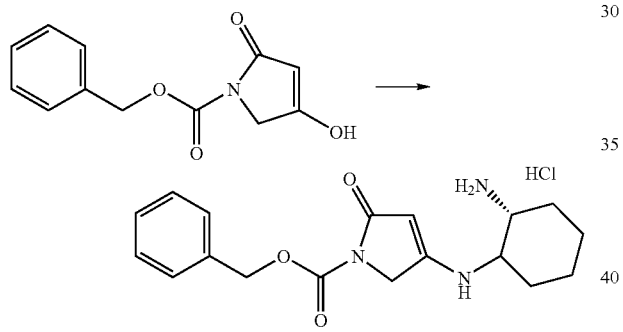

(1R,2R)-1,2-diaminocyclohexane 2294 g (20.09 mol) was dissolved in 3.1 L of ethanol to make a solution. To a 100 L glass lined reactor equipped with a stirrer, were added 26.8 L of ethyl acetate, 4635 g of 4-hydroxy-2-oxo-3-pyrroline-1-carboxylic acid benzyl ester (content: 96.2%, 19.12 mol) synthesized according to the methods of Non-Patent Reference 9 and 12.5 L of ethanol, furthermore, a previously prepared ethanol solution of (1R,2R)-1,2-diaminocyclohexane was added at 15 to 21° C. For washing, 2.2 L of ethanol was used. Next, 3.35 L of 6M hydrochloric acid (20.1 mol) was added at 19 to 25° C. For washing, 0.3 L of water was used. The reaction mixture was heated to 60° C., and reacted at the same temperature for 3 hours. While holding the temperature at approximately 60° C., 4.4 L of ethyl acetate was added, the mixture was cooled to 50° C., 2.4 g of seed crystal was added, and the solution was kept at 50° C. for one hour. While holding the temperature at approximately 50° C., 22.3 L of ethyl acetate was added over one hour, the solution was kept at 50° C. for one hour, cooling to 10° C. over 4.6 hours, and kept at 10° C. for another 10 hours. The deposited solid was separated with a centrifuge, and washed with 17.8 L of a cooled mixed solution of ethyl acetate-ethanol (volume ratio: 75:25). The obtained wet solid was dried under reduced pressure at 50° C. for 19 hours to obtain 6342 g of 4-[(1R,2R)-2-aminocyclohexylamino]-2-oxo-3-pyrroline-1-carboxylic acid benzyl ester hydrochloride.

Proton NMR (DMSO-d6; 400 MHz): δ 8.30 (br-s, 3H), 7.69 (d, J=8.7 Hz, 1H), 7.28 to 7.46 (m, 5H), 5.19 (m, 2H), 4.82 (s, 1H), 4.34 (d, J=16.3 Hz, 1H), 4.20 (d, J=16.3 Hz, 1H), 3.20 (m, 1H), 2.94 (m, 1H), 2.05 (br-d, 1H), 1.91 (br-s, 1H), 1.67 (br-s, 2H), 1.46 (m, 1H), 1.15 to 1.35 (m, 3H)

Mass spectrum (ESI): m/Z=330 [M+H]$^+$, 364 [M+Cl]$^-$

Example 21

Synthesis of 4-[(1R,2R)-2-aminocyclohexylamino]-3-pyrroline-2-one hydrochloride

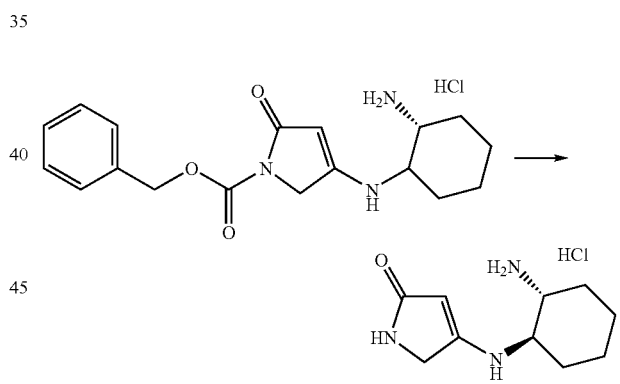

4-[(1R,2R)-2-aminocyclohexylamino]-2-oxo-3-pyrroline-1-carboxylic acid benzyl ester hydrochloride 13.0 g (35.5 mmol) was added with 50.3 mL of methanol and 1.58 g of 5% palladium carbon (moisture: 50%), and the mixture was stirred under hydrogen gas atmosphere at 25° C. for 3 hours. Palladium carbon was separated by filtration, washed with 13 mL of methanol, and the wash was pooled with filtrate. While stirring, this solution was added drop-wise with 60 mL of tetrahydrofuran at 30° C. over 30 minutes. The solution was cooled to 10° C. over 2 hours, and stirred at 10° C. overnight. The deposited solid was separated by filtration, and washed with 30 mL of methanol-tetrahydrofuran (volume ratio: 1:1) that was cooled to 10° C. Drying was carried out under reduced pressure at 50° C. overnight to obtain 7.50 g of solid. Furthermore, 7.0 g of this solid was dried under reduced pressure at 50° C. overnight to obtain 6.19 g of 4-[(1R,2R)-2-aminocyclohexylamino]-3-pyrroline-2-one hydrochloride.

Proton NMR (DMSO-d6; 400 MHz): δ8.19 (br-s, 3H), 6.87 (d, J=8.8 Hz, 1H), 6.66 (s, 1H), 4.57 (d, J=0.96 Hz, 1H), 3.83 (d, J=16.5 Hz, 1H), 3.73 (d, J=16.5 Hz, 1H), 3.08 (m, 1H), 2.91 (m, 1H), 2.04 (br-d, 1H), 1.93 (br-d, 1H), 1.67 (br-s, 2H), 1.44 (m, 1H), 1.13 to 1.33 (m, 3H)

Mass spectrum (ESI): m/Z=196 [M+H]$^+$, 230 [M+Cl]$^-$

In addition, by converting the source material benzyl ester hydrochloride to free form by a conventional method including liquid separation manipulation for extraction into organic solvent, and with this free form as source material, carrying out deprotection reaction by catalytic reduction similarly to the above, 4-[(1R,2R)-2-aminocyclohexylamino]-3-pyrroline-2-one can be obtained in free form (that is to say, not taking the morphology of salt).

Example 22

Preparation of 4-[(1R,2R)-2-aminocyclohexylamino]-3-pyrroline-2-one hydrochloride solution To 32 L of methanol, 3999 g of 4-[(1R,2R)-2-aminocyclohexylamino]-2-oxo-3-pyrroline-1-carboxylic acid benzyl ester hydrochloride and 486 g of 5% palladium carbon (moisture: 52%) were added, hydrogen gas blown in while vigorously stirring at 25° C. for 4.5 hours. When analyzed by high performance liquid chromatography, the source material 4-[(1R,2R)-2-aminocyclohexylamino]-2-oxo-3-pyrroline-1-carboxylic acid benzyl ester was not detected, and 4-[(1R,2R)-2-aminocyclohexylamino]-3-pyrroline-2-one hydrochloride was found to be generated quantitatively. Palladium carbon was separated by filtration using a pressure filter, washed with 8.0 L of methanol, and the wash and the filtrate were pooled to obtain a methanol solution of 4-[(1R,2R)-2-aminocyclohexylamino]-3-pyrroline-2-one hydrochloride.

In addition, the compounds for which the chemical structural formulae are shown below are readily prepared almost similarly to methods described in the previous examples or preparation methods, or by applying thereto slightly modified procedures obvious to those skilled in the art.

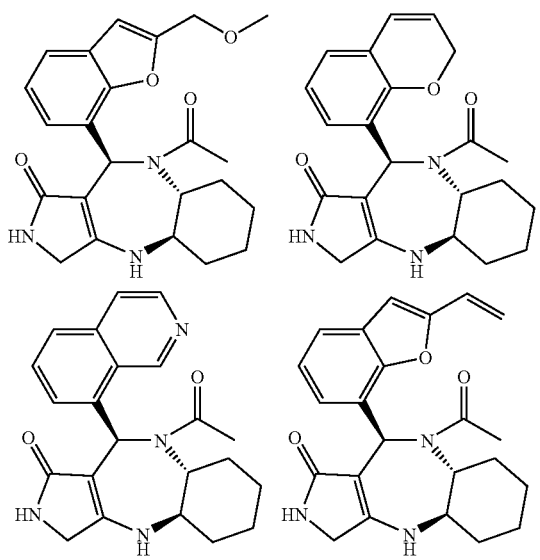

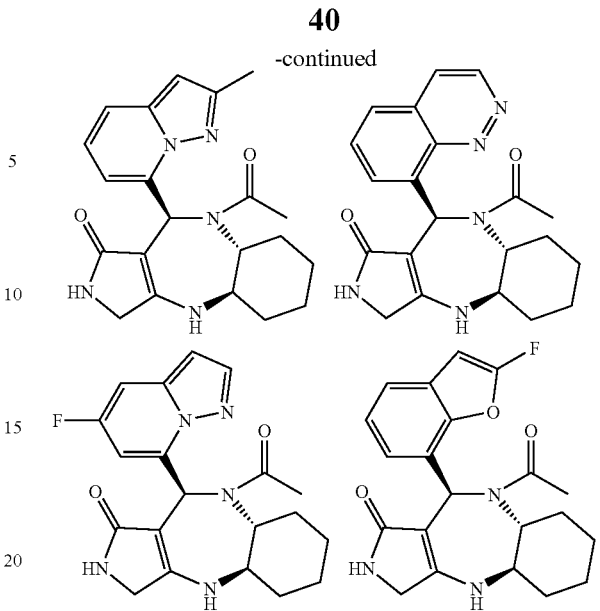

Test Example 1

Evaluation of Sugar Transport Activity

1. Acquisition of Rat Adipocytes

Three male Wistar rats (6 to 7 weeks old) were bled by decapitation, and then laparotomized to extract 3 g of paratesticular fat tissue. This was added with KRH (Krebs Ringer HEPES: composition, 130 mM sodium chloride, 4.7 mM potassium chloride, 1.2 mM potassium dihydrogen phosphate, 1.2 mM magnesium sulfate, 1 mM calcium chloride, 25 mM HEPES, pH=7.6) containing 2% BSA (bovine serum albumin) so that the total amount of adipocyte was 4 ml, and chopped with scissors for 5 minutes. An amount of 8 mg of collagenase (Type I) was added to carry out digestion treatment for 35 minutes, and undigested fragments were eliminated with a nylon mesh to obtain approximately 3 ml of isolated adipocytes. Collagenase was eliminated by buffer exchange, then, 2% BSA/KRH solution was added for resuspension to obtain 15 ml of adipocyte suspension.

2. Evaluation of Sugar Transport Activity

The evaluation of sugar transport activity of the compound of the present invention was carried out with the methods described in the literature (Annual Review of Biochemistry, Volume 55, Page 1059, 1986) as a reference. That is to say, the above adipocyte suspension was distributed into polystyrene test tube, 200 μl each, 100 μl of solution of test substance (10 mg/ml of dimethylsulfoxide solution diluted with KRH) was added, and cultured while shaking at 37° C. for 30 minutes.

The sugar transport activity was evaluated by measuring the amount of 2-[$^{14}$C (U)]-deoxy-D-glucose incorporated per time unit. That is to say, an adipocyte suspension for which the preculture was finished was added with 2-[$^{14}$C (U)]-deoxy-D-glucose (final concentration: 0.5 μCi/sample), and cytochalasin B (final concentration: 10 μM) was added after 5 minutes to stop sugar transport. Adipocytes and buffer were separated by laying over dinonyl phthalate and centrifuging, the amount of 2-[$^{14}$C (U)]-deoxy-D-glucose contained in the adipocyte layer was measured with a liquid scintillation counter, to quantify the amount of sugar incorporated. In the present evaluation system, insulin (100 nM), which has sugar transport enhancement action, exhibited on the order of 3-9 times enhancement action compare to non-insulin added control group.

The results of evaluation of sugar transport activity of the compound of the present invention are shown in Table 4. In the table, the sugar transport activity was determined as the concentration of test compound corresponding to 50% enhancement action (EC50: μg/ml) when the enhancement action of insulin (100 nM) is taken as 100%.

TABLE 4

| No. | EC50 (μg/ml) |
|---|---|
| 1 | 0.65 |
| 2 | 0.39 |
| 5 | 0.26 |
| 6 | 0.58 |
| 7 | 1.94 |
| 8 | 0.61 |
| 9 | 0.92 |
| 11 | 0.73 |
| 12 | 0.63 |
| 13 | 0.90 |
| 14 | 1.3 |
| 16 | 1.36 |
| 17 | 0.59 |
| 18 | 3.1 |
| 19 | 0.45 |

Test Example 2

Evaluation of Hypoglycemic Action in Pathologic Mouse or Rat

C57BL/KsJ-db/dbJcl mice (8 to 9 weeks old) or GK/Jcl rats fasted for 20 hours were administered with the test compound by a single oral administration, blood was collected from the tail vein immediately before administration and 30, 60, 120 and 180 minutes after administration, and the blood glucose level was measured with Fuji DryChem5500 (glucose oxidase method). For the test animals, a group comprised 4 to 5 subjects, and the blood glucose level was determined as mean values. The test compound was administered by dissolving in an aqueous solution of 50% polyethyleneglycol 400, or 100% polyethyleneglycol 400.

The degrees of hypoglycemia calculated based on the blood glucose levels measured according to the methods described above are shown in Table 5 (mouse) and Table 6 (rat). The degree of hypoglycemia was calculated as the percentage of the difference between the blood glucose level at one time point 120 minutes after administration and blood glucose level immediately before administration, with respect to the blood glucose level immediately before administration.

In addition (star) is the compound of Example 129 in WO02/44180 (Patent Reference 1) [same as compound in Example 129 of US2004/0048847 (Patent Reference 2), and compound of Example 1 (II) in WO2004/069259 (Patent Reference 3)].

TABLE 5

Degree of hypoglycemia in C57BL/KsJ-db/dbJcl mouse (%)

| Example No. | Dosage (mg/kg) | | | |
|---|---|---|---|---|
| | 100 | 30 | 10 | 3 |
| 1 | — | — | 51 | 4 |
| 5 | — | — | 41 | 28 |
| 8 | — | — | 23 | 26 |
| 16 | — | — | 36 | 12 |
| 18 | — | — | 41 | 21 |
| 19 | — | — | 36 | 31 |
| * | 64 | 30 | 16 | — |

—: not evaluated

TABLE 6

Degree of hypoglycemia in GK/Jcl rat (%)

| Example No. | Dosage (mg/kg) | | | |
|---|---|---|---|---|
| | 100 | 30 | 10 | 3 |
| 2 | — | — | 43 | — |
| 9 | — | — | 37 | 30 |
| 12 | — | — | 34 | — |
| 14 | — | — | 36 | — |
| 17 | — | — | 35 | — |
| * | 38 | 22 | — | — |

—: not evaluated

Example 3

Evaluation of Membrane Permeability

The compound of the present invention was evaluated for membrane permeability using MDCK cells, according to the method below. The membrane permeability is thought to reflect satisfactorily the permeability-absorbability in the human intestinal tract. The results are shown in Table 7.

(Method)

An epithelial cell line derived from dog renal tubule, MDCK (Madin Darby Canine Kidney cell line), is cultured for 3 to 4 days in a flask containing 10% FBS-added D-MEM/F12 culture medium (Manufactured by Gibco) at 37° C. in a carbon dioxide incubator. The cells are detached from the flask with a Trypsin/EDTA solution (Manufactured by Gibco), and unicellularized by pipetting. The cells are suspended in the same medium as described above and placed in a transwell (mucous membrane-side well) of a Transwell plate (manufactured by COSTAR) at $2 \times 10^5$ cell/well in a volume of 0.1 ml. The transwell is transferred to the basal membrane-side well where 0.6 ml of the same culture medium has been placed, and the cells are cultured at 37° C. in a carbon dioxide incubator for 3 days. After the culture, the culture media in the mucous membrane-side well and the basal membrane-side well are exchanged for the same culture medium, incubated under the same condition for one day. Thus, satisfactory MDCK monolayer culture cells are obtained.

During in vitro permeation-absorption experiments, the culture media are eliminated from both wells, the mucous membrane-side well is washed with PBS buffer solution (pH 6.5), and the basal membrane-side well is washed with PBS buffer solution (pH 7.4). Next, 0.1 ml of PBS buffer solution (pH6.5) is added to the mucous membrane-side well, 0.6 ml of PBS buffer solution (pH 7.4) is added to the basal membrane-side well, and equilibration is carried out by incubating for 15 minutes in a 37° C. incubator.

The mucous membrane-side well is exchanged for 0.1 ml of a solution containing the test substance prepared with PBS buffer solution (pH6.5), and time point when the well is transferred to the basal membrane-side well substituted with 0.6 ml of PBS buffer solution (pH7.4) is taken as the permeation-absorption start time, and thereafter, sampling is performed from the basal membrane-side well over time. The amounts of test substance in the samples sampled in this way are measured by HPLC analysis, and the amount of the substance permeated and absorbed from the mucous membrane side to the basal membrane side according to the reaction time is determined to determine the permeation coefficient (cm/sec).

(Results)

TABLE 7

| Example | Permeation coefficient ($10^{-7}$ cm/sec) |
|---|---|
| 1 | 8 |
| 2 | 10 |
| 5 | 20 |
| 6 | 8 |
| 9 | 40 |
| 12 | 20 |
| 16 | 9 |
| 17 | 10 |
| 19 | 10 |

As is clear from the above results, the compound of the present invention has sugar transport enhancement action and exhibit excellent hypoglycemic action at low doses, such that it is thought to become a therapeutic agent useful against diabetes mellitus, diabetic peripheral neuropathy, diabetic nephropathy, diabetic retinopathy, diabetic macrovascular disease, glucose tolerance anomaly, or obesity.

Note that the excellent hypoglycemic action of the compound of the present invention can also be evaluated similarly to the above, using a normal mouse or a KK-Ay/Ta Jcl mouse.

Furthermore, the compound of the present invention has excellent membrane permeability. It exhibits high absorbability in oral administration, and is thought to become an orally administered agent having little variation within an individual or between individuals, which is easy to use.

Numerous modifications and variations on the present invention are possible in light of the above teachings. It is, therefore, to be understood that within the scope of the accompanying claims, the invention may be practiced otherwise than as specifically described herein.

The invention claimed is:

1. A lactam compound, or a pharmaceutically acceptable salt thereof, represented by Formula (1):

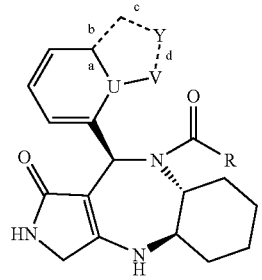

(1)

wherein R is selected from the group consisting of a lower alkyl group, a lower alkenyl group, a lower alkynyl group or a lower alkoxy group, which may have one to three substituents, Y is either N or CR', with the proviso that when the bonds indicated by c and d are both single bonds Y is either NH or CHR', R' is selected from the group consisting of a hydrogen atom, a lower alkyl group, a lower alkenyl group, a lower alkynyl group, a lower alkoxy group, a lower alkylthio group, a lower alkylamino group, a halogen group, a nitro group, and a cyano group, which may have one to three substituents, U represents C or N, in regard to the bonds indicated by a, b, c and d, and V, i) when U represents C, a represents a double bond, b and d represent single bonds, and c represents either a single bond or a double bond, V represents —X—, or —CH$_2$—O—, —O—CH$_2$—, —CH=N—, —N=N— or —N=CH— from the side of Y, ii) when U represents N, a and c represent single bonds, b and d represent double bonds, V represents —N—, or —CH—X— from the side of Y, X represents O, S or NH, and the bicyclic fused ring containing U may be substituted with one to three fluorine atoms:

wherein said substituent is selected from the group consisting of a halogen, a hydroxyl, a methoxy, an ethoxy, an acetoxy, a methylthio, a methane sulfonyl group, an amino group, a methylamino group, a dimethylamino group, an acetylamino group, and a methoxy carbamoyl group.

2. The lactam compound, or pharmaceutically acceptable salt thereof, according to claim 1, wherein said lactam compound is represented by Formula (1-1):

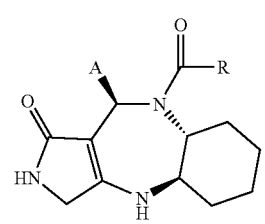

(1-1)

wherein R is a lower alkyl group or a lower alkoxy group, which may be substituted with one to three substituents, and A is an organic group selected from Formulae (2) to (7):

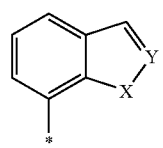 (2)

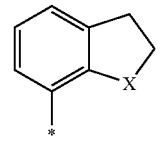 (3)

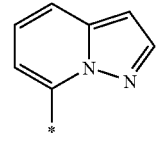 (4)

 (5)

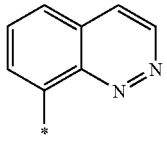 (6)

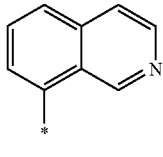 (7)

wherein, in Formulae (2) and (3),

X is selected from the group consisting of O, S and NH,

Y is N or CR', wherein R' is selected from the group consisting of a hydrogen atom, a lower alkyl group, a lower alkenyl group, a lower alkynyl group, a lower alkoxy group, a lower alkylthio group, a lower alkylamino group, a halogen group, a nitro group, and a cyano group, which may have one to three substituents, and wherein said substituent is selected from the group consisting of a halogen, a hydroxyl, a methoxy, an ethoxy, an acetoxy, a methylthio, a methane sulfonyl group, an amino group, a methylamino group, a dimethylamino group, an acetylamino group, and a methoxy carbamoyl group.

3. The lactam compound, or a pharmaceutically acceptable salt thereof, according to claim 2, wherein R is selected from the group consisting of a methyl group, an ethyl group, a cyclopropyl group, a hydroxymethyl group, a methoxymethyl group, a difluoromethyl group, a trifluoromethyl group or a methoxy group.

4. The lactam compound, or a pharmaceutically acceptable salt thereof, according to claim 2, wherein A is an organic group selected from the group consisting of Formula (2), Formula (3), Formula (4), and Formula (5).

5. The lactam compound, or a pharmaceutically acceptable salt thereof, according to claim 2, wherein A is the organic group represented by Formula (2), wherein Y is CR'.

6. The lactam compound, or a pharmaceutically acceptable salt thereof, according to claim 2, wherein A is the organic group represented by Formula (2), wherein Y is CR' and R' is a hydrogen atom or a lower alkyl group.

7. The lactam compound, or a pharmaceutically acceptable salt thereof, according to claim 2, wherein A is the organic group represented by Formula (5).

8. The lactam compound, or a pharmaceutically acceptable salt thereof, according to claim 2, wherein said lactam compound is selected from the compounds represented by Formulae (a) to (j):

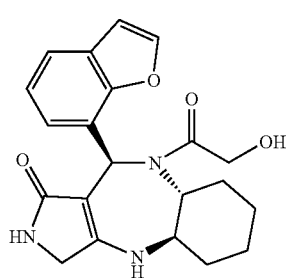 (a)

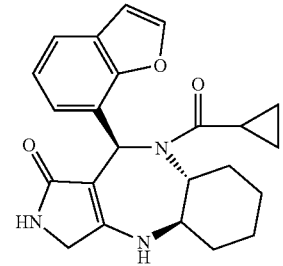 (b)

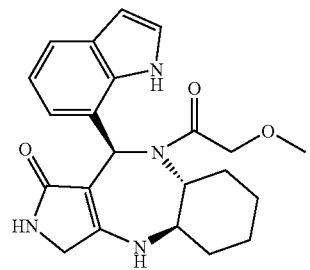 (c)

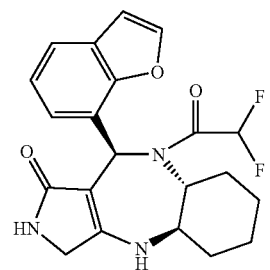 (d)

(e)
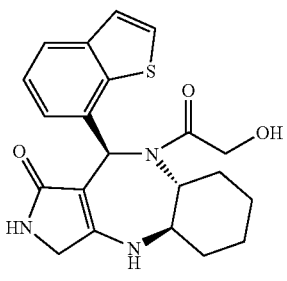

(f)
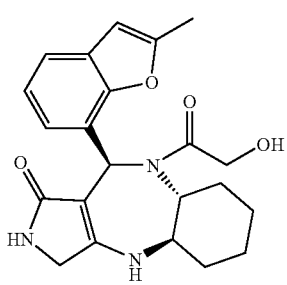

(g)
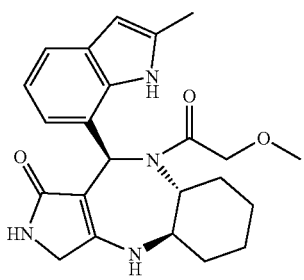

(h)
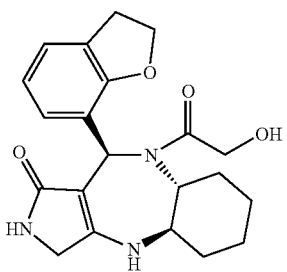

(i)
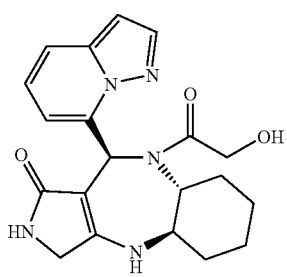

(j)
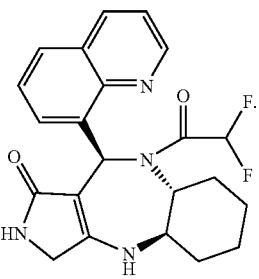

9. The lactam compound, or a pharmaceutically acceptable salt thereof, according to claim 8, wherein said lactam compound is the compound represented by Formula (a).

10. The lactam compound, or a pharmaceutically acceptable salt thereof, according to claim 8, wherein said lactam compound is the compound represented by Formula (b).

11. The lactam compound, or a pharmaceutically acceptable salt thereof, according to claim 8, wherein said lactam compound is the compound represented by Formula (c).

12. The lactam compound, or a pharmaceutically acceptable salt thereof, according to claim 8, wherein said lactam compound is the compound represented by Formula (d).

13. The lactam compound, or a pharmaceutically acceptable salt thereof, according to claim 8, wherein said lactam compound is the compound represented by Formula (e).

14. The lactam compound, or a pharmaceutically acceptable salt thereof, according to claim 8, wherein said lactam compound is the compound represented by Formula (f).

15. The lactam compound, or a pharmaceutically acceptable salt thereof, according to claim 8, wherein said lactam compound is the compound represented by Formula (g).

16. The lactam compound, or a pharmaceutically acceptable salt thereof, according to claim 8, wherein said lactam compound is the compound represented by Formula (h).

17. The lactam compound, or a pharmaceutically acceptable salt thereof, according to claim 8, wherein said lactam compound is the compound represented by Formula (1).

18. The lactam compound, or a pharmaceutically acceptable salt thereof, according to claim 8, wherein said lactam compound is the compound represented by Formula (j).

19. A pharmaceutical composition comprising the lactam compound or a pharmaceutically acceptable salt thereof according to claim 1 and at least one formulation carrier.

20. A method for treating a disorder selected from the group consisting of diabetes mellitus, diabetic peripheral neuropathy, diabetic nephropathy, diabetic retinopathy, diabetic macrovascular disease, glucose tolerance anomaly, and obesity, comprising administering an effective amount of the pharmaceutical composition according to claim 19 to a subject in need thereof.

21. A lactam compound, or a pharmaceutically acceptable salt thereof, represented by Formula (1-2):

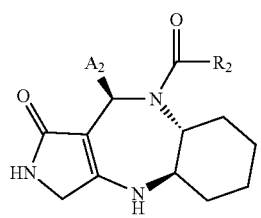

(1-2)

wherein $R_2$ is selected from the group consisting of a methyl group, an ethyl group, a cyclopropyl group, a hydroxymethyl group, a methoxymethyl group, a difluoromethyl group, a trifluoromethyl group, and a methoxy group, and
$A_2$ is represented by either Formula (2-2) or Formula (3-2):

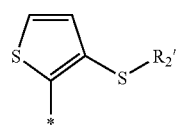

(2-2)

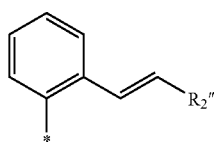

(3-2)

wherein
$R_2'$ is a lower alkyl group and
$R_2''$ is a hydrogen atom or a lower alkyl group.

22. The lactam compound, or a pharmaceutically acceptable salt thereof, according to claim 21, wherein said lactam compound is selected from the compounds represented by the following formulae

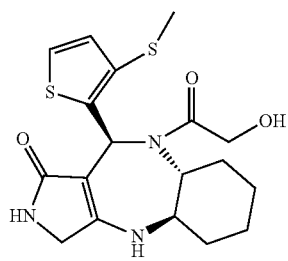

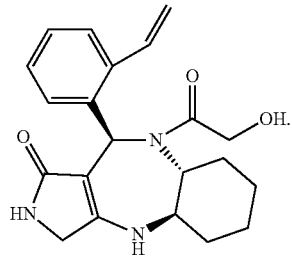

23. A pharmaceutical composition comprising the lactam compound or a pharmaceutically acceptable salt thereof according to claim 21 and at least one formulation carrier.

24. A method for treating a disorder selected from the group consisting of diabetes mellitus, diabetic peripheral neuropathy, diabetic nephropathy, diabetic retinopathy, diabetic macrovascular disease, glucose tolerance anomaly, and obesity, comprising administering an effective amount of the pharmaceutical composition according to claim 23 to a subject in need thereof.

25. A method of producing a lactam compound, or pharmaceutically acceptable salt thereof, wherein said lactam compound is represented by Formula (1-1):

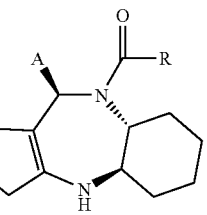

(1-1)

wherein R is a lower alkyl group or a lower alkoxy group, which may be substituted with one to three substituents, and
A is an organic group selected from Formulae (2) to (7):

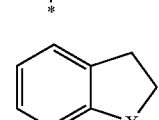

(2)

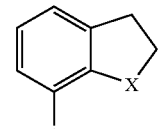

(3)

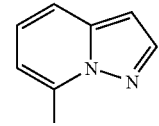

(4)

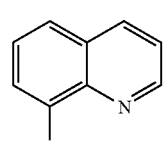

(5)

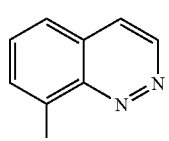

(6)

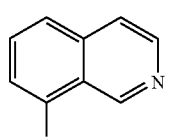

(7)

wherein, in Formulae (2) and (3),
X is selected from the group consisting of O, S and NH,
Y is N or CR', wherein R' is selected from the group consisting of a hydrogen atom, a lower alkyl group, a lower alkenyl group, a lower alkynyl group, a lower alkoxy group, a lower alkylthio group, a lower alkylamino group, a halogen group, a nitro group, and a cyano group, which may have one to three substituents, and
wherein said substituent is selected from the group consisting of a halogen, a hydroxyl, a methoxy, an ethoxy, an acetoxy, a methylthio, a methane sulfonyl group, an amino group, a methylamino group, a dimethylamino group, an acetylamino group, and a methoxy carbamoyl group;
said method comprising
(i) reacting 4-[(1R,2R)-2-aminocyclohexylamino]-3-pyrroline-2-one represented by formula (8) with an aldehyde represented by formula (9) to produce cyclized compound (10), and
(ii) acylating said cyclized compound (10) under conditions selected from the group consisting of
reacting said cyclized compound (10) with a carboxylic acid, RCOOH, using the condensation agent 1-[3-(dimethylamino)propyl]-3-ethylcarbodiimide hydrochloride;
reacting said cyclized compound (10) with a carboxylic acid, RCOOH, using the condensation agent 1-[3-(dimethylamino)propyl]-3-ethylcarbodiimide hydrochloride, followed by subjecting the reaction products to basic treatment in the presence of methanol;
reacting said cyclized compound (10) with an acid anhydride, $(RCO)_2O$, derived from a carboxylic acid, RCOOH, in the presence of pyridine, followed by subjecting the reaction products to basic treatment in the presence of methanol; and
reacting said cyclized compound (10) with an alkyl chloroformate in a hydrous solvent under basic conditions

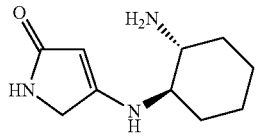

(8)

(9)

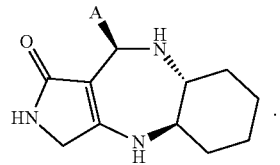

(10)

* * * * *